(12) United States Patent
Jin et al.

(10) Patent No.: US 10,507,426 B2
(45) Date of Patent: *Dec. 17, 2019

(54) SYSTEMS AND METHODS FOR BIOLOGICAL CONVERSION OF CARBON DIOXIDE POLLUTANTS INTO USEFUL PRODUCTS

(71) Applicant: The University of Wyoming Research Corporation, Laramie, WY (US)

(72) Inventors: Song Jin, Fort Collins, CO (US); Paul Fallgren, Westminster, CO (US); Jeffrey M Morris, Arvada, CO (US); Alan E Bland, Laramie, WY (US); Patrick Richards, Seattle, WA (US); Jesse D Newcomer, Laramie, WY (US); Patricia Colberg, Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 23 days.

This patent is subject to a terminal disclaimer.

(21) Appl. No.: 15/707,780

(22) Filed: Sep. 18, 2017

(65) Prior Publication Data

US 2018/0001256 A1 Jan. 4, 2018

Related U.S. Application Data

(63) Continuation of application No. 13/792,144, filed on Mar. 10, 2013, now Pat. No. 9,764,279, which is a (Continued)

(51) Int. Cl.
*B01D 53/62* (2006.01)
*B01D 53/84* (2006.01)
(Continued)

(52) U.S. Cl.
CPC ............. *B01D 53/62* (2013.01); *B01D 53/84* (2013.01); *C10L 1/026* (2013.01); *C12N 1/20* (2013.01);
(Continued)

(58) Field of Classification Search
None
See application file for complete search history.

(56) References Cited

U.S. PATENT DOCUMENTS

| 4,760,027 A | 7/1988 | Sublette |
| 5,173,429 A | 12/1992 | Gaddy et al. |

(Continued)

FOREIGN PATENT DOCUMENTS

| CA | 2803091 | 5/2018 |
| EP | 0218958 A2 | 4/1987 |

(Continued)

OTHER PUBLICATIONS

U.S. Appl. No. 13/792,138, filed Mar. 10, 2013. First Named Inventor: Song Jin. Non-Final Office Action dated Mar. 23, 2016. 8 pages.

(Continued)

*Primary Examiner* — David W Berke-Schlessel
(74) *Attorney, Agent, or Firm* — Santangelo Law Offices, P.C.

(57) ABSTRACT

Methods and systems to achieve clean fuel processing systems in which carbon dioxide emissions (1) from sources (2) may be processed in at least one processing reactor (4) containing a plurality of chemoautotrophic bacteria (5) which can convert the carbon dioxide emissions into biomass (6) which may then be used for various products (21) such as biofuels, fertilizer, feedstock, or the like. Sulfate reducing bacteria (13) may be used to supply sulfur containing compounds to the chemoautotrophic bacteria (5).

15 Claims, 9 Drawing Sheets

Related U.S. Application Data continuation of application No. 13/127,697, filed as application No. PCT/US2010/043392 on Jul. 27, 2010, now abandoned.

(60) Provisional application No. 61/358,700, filed on Jun. 25, 2010, provisional application No. 61/228,898, filed on Jul. 27, 2009.

(51) Int. Cl.
   *C12N 1/20* (2006.01)
   *C12P 7/64* (2006.01)
   *F23J 15/02* (2006.01)
   *C10L 1/02* (2006.01)

(52) U.S. Cl.
   CPC .............. *C12P 7/649* (2013.01); *F23J 15/02* (2013.01); *B01D 2251/95* (2013.01); *B01D 2257/504* (2013.01); *C10G 2300/1011* (2013.01); *C10G 2300/405* (2013.01); *C10G 2300/4043* (2013.01); *F23J 2215/50* (2013.01); *Y02A 50/2358* (2018.01); *Y02C 10/02* (2013.01); *Y02C 10/04* (2013.01); *Y02E 20/326* (2013.01); *Y02E 50/13* (2013.01); *Y02E 50/17* (2013.01); *Y02E 50/343* (2013.01); *Y02E 50/346* (2013.01); *Y02P 20/152* (2015.11); *Y02P 20/59* (2015.11); *Y02P 30/10* (2015.11); *Y02P 30/20* (2015.11); *Y02P 30/446* (2015.11)

(56) References Cited

U.S. PATENT DOCUMENTS

| | | | |
|---|---|---|---|
| 5,593,886 | A | 1/1997 | Gaddy |
| 5,981,266 | A | 11/1999 | Srivastava et al. |
| 7,285,402 | B2 | 10/2007 | Gaddy et al. |
| 7,832,475 | B2 | 11/2010 | Jin et al. |
| 8,127,839 | B2 | 3/2012 | Jin et al. |
| 9,764,279 | B2 | 9/2017 | Jin et al. |
| 2003/0002236 | A1 | 1/2003 | Parent et al. |
| 2003/0022364 | A1 | 1/2003 | Parent et al. |
| 2003/0066322 | A1 | 4/2003 | Perriello |
| 2010/0120104 | A1 | 5/2010 | Reed |
| 2012/0003705 | A1 | 1/2012 | Jin et al. |
| 2013/0189739 | A1 | 7/2013 | Jin et al. |
| 2013/0189750 | A1 | 7/2013 | Jin et al. |

FOREIGN PATENT DOCUMENTS

| | | |
|---|---|---|
| WO | 2007109066 A1 | 9/2007 |
| WO | 2008128331 A1 | 10/2008 |
| WO | 2009001424 A1 | 12/2008 |
| WO | 2009002772 A1 | 12/2008 |
| WO | 2011014507 A1 | 2/2011 |
| WO | 2011056183 A1 | 5/2011 |

OTHER PUBLICATIONS

Australian Patent Application No. 2010276503, Notice of Acceptance dated Mar. 14, 2015. 3 pages.

U.S. Appl. No. 13/508,472, filed Dec. 4, 2012. First Named Inventor: Reed.

European Patent Application No. 10804958.6, extended Search Report dated Jun. 4, 2014, 7 pages.

Australian Patent Application No. 2010276503, Patent Examination Report No. 1 dated Jun. 6, 2013, 3 pages.

Kwak et al, "Optimization of culture conditions for CO2 fixation by a chemoautotrophic microorganism, strain YN-1 using factorial design" Biochemical Engineering Journal vol. 31 No. 1, Aug. 1, 2006; 8 pages.

Akoh, C.C., S. Chang, G. Lee and J. Shaw, "Enzymatic approach to biodiesel production," J. Agric. Food Chem., 55, 8995-9005, 2007.

Antoni, D., V. V. Zverlov, and W. H. Schwarz, "Biofuels from microbes," Appl. Microbiol. Biot., 77, 23-35, 2007.

Bland, A., J. Newcomer, T. Zhang, K. Sellakumar, "Pilot testing of WRI's novel mercury control technology by pre-combustion thermal treatment of coal", Report to U.S. Department of Energy, Contract No. DE-FC26-98FT40323 Task 79, Jun. 2009.

Certick, M. and S. Shimizu, "Review: biosynthesis and regulation of microbial polyunsaturated fatty acid production," J. Biosci. Bioeng., 87, 1-14, 1999.

Certik, M. and R. Horenitzky, "Supercritical CO2 extraction of fungal oil containing □-linolenic acid," Biotechnol. Tech., 13, 11-15, 1999.

Chen, G., "A microbial polyhydroxyalkanoates (PHA) based bio- and materials industry," Chem. Soc. Rev., 38, 2434-2446, 2009.

Ciferno, J., "Pulverized coal oxycombustion power plants—final results" (revised), U.S. Department of Energy, National Energy Technology Laboratory, Nov. 1, 2007.

Cooney, M. J., E. Roschi, I. W. Marison, C. Comninellis, and U. Von Stockar, "Physiologic studies with the sulfate-reducing bacterium Desulfovibrio desulfuricans: Evaluation for use in a biofuel cell," Enzym. Microb. Tech., 8, 358-365, 1996.

Dasu, B. N., and K. L. Sublette, "Microbial Removal of sulfur dioxide from a gas stream with net oxidation to sulfate," Appl. Biochem. Biotech., vol. 20/21, 207-220, 1989.

Davis, J.B., "Paraffinic hydrocarbons in the sulfate reducing bacterium desulfovibrio desulfuricans," Chem. Geol., 3, 155-160, 1968.

Dhar, B. R., and K. Kirtania, "Excess methanol recovery in biodiesel production process using a distillation column: a simulation study," Chemical Engineering Research Bulletin, 13, 45-50, 2009.

DOE/NETL, "Cost and performance baseline for fossil energy plants—vol. 1: bituminous coal and natural gas to electricity," DOE/NETL-2007/1281, May 2007, Revision 1, Aug. 2007.

Cantisan, S, Garces, R., Alvarez-Ortega, R., Martinez-Force, E., "Lipid characterization in vegetative tissues of high saturated fatty acid sunflower mutants," J. Agric. Food Chem., 47, 78-82, 1999.

Green Econometrics, "Understanding the cost of solar energy," http://greenecon.net/understanding-the-cost-of-solar-energy/energy_economics.html, 2007.

GTM Research, "Transitioning from 1st generation to advanced biofuels," a white paper from Enterprise Florida and GTM Research, Feb. 2010.

Kelly, D.P, "Thermodynamic aspects of energy conservation by chemolithotrophic sulfur bacteria in relation to the sulfur oxidation pathways," Arch Microbial, 171, 219-229, 1999.

Li, Q., W. Du, and D. Liu, "Perspectives of microbial oils for biodiesel production," Appl. Microbiol. Biot., 80, 749-756, 2008.

Gouda, M., Omar, S, Aousadi L, "Single cell oil production by Gordonia sp. DG using agro-industrial wastes," World J. Microbiol. Biotechnol., 24, 1703-1711, 2008.

Monteiro, M. R., A. R. P. Ambrozin, L. M. Lião, and A. G. Ferreira, "Critical review on analytical methods for biodiesel characterization," Talanta, 77, 593-605, 2008.

Parawira, W., "Biotechnological production of biodiesel fuel using biocatalysed transesterification: A review," Cr. Rev. Biotechn., 29, 82-93, 2009.

Rabus, R., T.A. Hansen and F. Widdel, "Dissimilatory sulfate- and sulfur-reducing prokaryotes," Prokaryotes, 2, 659-768, 2006.

Scott, K. M., and C. M.Cavanaugh, "CO2 uptake and fixation by endosymbiotic chemoautotrophs from the bivalve Solemya velum," Appl. Environ. Microb., 73, 1174-1179, 2007.

Shively, J. M., G. van Keulen, and W. G. Meijer, "Something from almost nothing: carbon dioxide fixation in chemoautotrophs," Annu. Rev. Microbiol, 52, 191-230, 1998.

Thurmond, W., Algae 2020: Algal Biofuels Demand Drivers, Players, Business Models, Markets & Commercialization Outlook, 1st edition, 2009, www.emerging-market.com.

Van Lier, R.J.M., C.J.N. Buisman, and N.L. Piret, "THIOPAQ® technology: versatile high-rate biotechnology for the mining and metallurgical industries," Proceedings of the Tms Fall Extraction and Processing Conference, v 3, p. 2319-2328, 1999.

(56) References Cited

OTHER PUBLICATIONS

Yuan, W., A. C. Hansen, and Q. Zhang, "Predicting the physical properties of biodiesel for combustion modeling," T. ASAE, 46, 1487-1493, 2003.
Zhang, T., and L. T. Fan, "Significance of dead-state-based thermodynamics in designing a sustainable process," Design for Energy and the Environment—Proceedings of the Seventh International Conference on the Foundations of Computer-Aided Process Design, Eds., M. M. El-Halwagi and A. A. Linninger, CRC Press, Boca Raton, FL, pp. 233-241, 2010.
Zhang, X., R. Luo, Z. Wang, Y. Deng, and G. Chen, "Application of (R)-3-hydroxyalkanoate methyl esters derived from microbial polyhydroxyalkanoates as novel biofuels," Biomacromolecules, 10, 707-711, 2009.
Chen, K.S., and E.E. Kalu, "Final report on LDRD project: Biodiesel production from vegetable oils using slit-channel reactors," Sandia report, SAND2008-0213, 2008.
Ehimen, E. A., "Energy Balance of Microalgal-derived Biodiesel," Energy Sources, Par A: Recovery, Utilization, and Environmental Effects, 32, 1111-1120, 2010.
Lawford, H. G., and J. D. Rousseau, "Studies on nutrient requirements and cost-effective supplements for ethanol production by recombinant E. coli," Applied biochemistry and biotechnology, 57158, 307-326.
Madigan, M. T., J. M. Martinko, J. Parker, Brock Biology of Microorganisms, Prentice Hall, 12th Edition, 2009.
Nagpal, S., S. Chuichulcherm, A. Livingston, and L. Peeva, "Ethanol utilization by sulfate-reducing bacteria: an experimental and modeling study,"Biotechnology and Bioengineering, 70, 533-543, 2000.
Lardon, L., A. Helias, B Sialve, J. Steyer, and O. Bernard, "Lifecycle assessment of biodiesel production from microalgae," Policy Analysis, 43, 6475-6481, 2009.
Shieh, J.H. and L.T. Fan, "Estimation of Energy (Enthalpy) and Exergy (Availability) Contents in Structurally Complicated Materials," Energy Sources, 6, 1 46 (1982).
International Application No. PCT/US2010/043392; International Search Report dated Sep. 21, 2010.
International Application No. PCT/US2010/043392; Written Opinion of the International Searching Authority dated Sep. 21, 2010.
U.S. Appl. No. 61/228,898, filed Jul. 27, 2009. First Named Inventor: Jin.
U.S. Appl. No. 61/358,700, filed Jun. 25, 2010. First Named Inventor: Bland.
White Paper: Transitioning From First Generation to Advanced Biofuels; Enterprise Florida and GTM Research, Feb. 2010, 15 pages.
Suzuki, I. and Werkman, C.H.; Chemautotropic Carbon Dioxide Fixation by Extracts of Thiobacillus Thiooxidans I. Formation of Oxalacetic Acid, Iowa State College, Oct. 16, 1957; 9 pages.
U.S. Appl. No. 12/613,550, filed Nov. 6, 2009. First Named Inventor: Reed.
U.S. Appl. No. 12/613,550, filed Nov. 6, 2009. First Named Inventor: Reed. Office Action dated Jun. 6, 2012. 12 pages.
U.S. Appl. No. 61/111,794, filed Nov. 6, 2008. First Named Inventor: Reed.
European Patent Application No. 10804958.6, Office Action dated Mar. 4, 2017, 6 pages.
European Patent Application No. 10804958.6, Notice of Allowance dated Sep. 5, 2018, 114 pages.
Canadian Patent Application No. 2803091, Notice of Allowance dated Aug. 22, 2017, 1 page.
Canadian Patent Application No. 2803091, Office Action dated Apr. 24, 2017, 3 pages.
Canadian Patent Application No. 2803091, Office Action dated Jul. 5, 2016, 3 pages.
U.S. Appl. No. 61/111,794, filed Nov. 6, 2008.
U.S. Appl. No. 13/127,697, filed May 4, 2011. First Named Inventor: Jin.
Kuenen, J.G. and Bos, P; "Habits and Ecological Niches of Chemolitho(auto)trophic Bacteria," Autotrophic Bacteria, Brock/Springer Series in Contemporary Bioscience, Delft University of Technology; pp. 53-59.
Madigan, Michael T, et al; Brock Biology of Microorganisms, 5.6 Oxidation-Reduction pp. 566-567.
Maier, Raina M. et al; Environmental Microbiology; 2.2 Bacteria, p. 27.
Prescott Harley Klein, Microbiology, Sixth Edition, Chapter 5, Microbial Nutrition p. 96; Chapter 8 Oxidation-Reduction Reactions and Electron Carriers, p. 153; Chapter 9 Metabolism: Energy Release and Conservation, p. 188; Glossary p. G-5.
VanLoon, W and Duffy, S; Environmental Chemistry, a global perspective; Second Edition; Chapter 11.2 Gases that React with Water; p. 241.
Kuenen, J.G. et al, Microbiology of Thiobacilli and Other Sulphur-Oxidizing Autotrophs, Mixotrophs and Heterotrophs [and Discussion]. Phil. Trans. R. Soc. Lond. B 1982 298. Published Sep. 13, 1982. 7 pages.
Taylor, et al. The Cellular Fatty Acids of the Sulphate-reducing Bacteria, *Desulfobacter* sp., *Desulfobulbus* sp. and Desulfovibrio desulfuricans. Journal of General Microbiology (1983) 129, 3303-3309. 7 pages.
Trudinger, P.A. Fixation of Carbon Dioxide by Extracts of the Strict Autotroph Thiobacillus denitrilicans. Department of Microbiology and A.R.C. Unit for Microbiology, University of Sheffield. Dec. 12, 1955. 13 pages.
U.S. Appl. No. 13/792,144, filed Mar. 10, 2013. First Named Inventor: Jin. Office Action dated Jan. 31, 2014.
Lynd, Lee R, et al. Fuel Ethanol from Cellulosic Biomass. Science, 251, 1318-1323, 1991.
U.S. Appl. No. 13/792,144, filed Mar. 10, 2013. First Named Inventor: Jin. Office Action dated Sep. 7, 2016. 12 pages. [Need Art Therein].
U.S. Appl. No. 13/792,144, filed Mar. 10, 2013. First Named Inventor: Jin. Office Action dated Sep. 9, 2014. 15 pages.
U.S. Appl. No. 13/792,144, filed Mar. 10, 2013. First Named Inventor: Jin. Office Action dated Nov. 30, 2015. 15 pages.
Cuffe, ST et al: "Air Pollutant Emissions from Coal-Fired Power Plants No. 1" Journal of Air Pollution Control Association, 14, 353-362, 1964.
U.S. Appl. No. 13/792,144, filed Mar. 10, 2013. First Named Inventor: Jin. Notice of Allowance dated May 23, 2017. 11 pages.
U.S. Appl. No. 13/792,144, filed Mar. 10, 2013. First Named Inventor: Jin. Restriction Requirement dated Oct. 10, 2013. 7 pages.

SYSTEMS AND METHODS FOR BIOLOGICAL CONVERSION OF CARBON DIOXIDE POLLUTANTS INTO USEFUL PRODUCTS

PRIORITY CLAIM

This application is a continuation of application Ser. No. 13/792,144 filed Mar. 10, 2013, issued as U.S. Pat. No. 9,764,279 on Sep. 19, 2017, which is a continuation of U.S. National Stage application Ser. No. 13/127,697 filed May 4, 2011, which claims priority to and the benefit of International Application Number PCT/US2010/043392 filed Jul. 27, 2010 which claims priority to and the benefit of U.S. Provisional Application No. 61/228,898 filed Jul. 27, 2009 and U.S. Provisional Application No. 61/358,700 filed Jun. 25, 2010, each hereby incorporated by reference herein.

This application relates to work performed under U.S. DOE Cooperative Agreement #DE-FC26-08NT43293. The U.S. government may have certain rights in this inventive technology, including "march-in" rights, as provided for by the terms of U.S. DOE Cooperative Agreement Numbers DOE #DE-FC26-08NT43293.

TECHNICAL FIELD

This invention relates to the technical field of clean processing systems, specifically, methods and apparatus for capturing and converting carbon dioxide emissions from fossil fuel consumption sources or other industrial carbon dioxide emitters. Through perhaps the use of chemoautotrophic bacteria, the invention provides apparatus and methods that can be used to capture and reduce carbon dioxide emissions into the atmosphere.

BACKGROUND OF THE INVENTION

Carbon sequestration is a topic receiving enormous attention in the media and among government agencies and industries involved in fossil fuel production and use. Combustion of fossil fuels is responsible for approximately 83% of greenhouse gas emissions in the U.S. Currently, the U.S. emits $6.0 \times 10^9$ tons carbon dioxide per year and this value is expected to increase by 27% over the next 20 years. Furthermore, the reported link between increasing concentrations of greenhouse gases such as carbon dioxide ($CO_2$) in the atmosphere and global climate change has prompted several countries to adopt environmental standards that cap $CO_2$ emissions and aim to reduce current emissions. Although the U.S. has not adopted a similar set of standards, in April 2007, the U.S. Supreme Court ruled that carbon dioxide was a pollutant and that the U.S. Environmental Protection Agency (U.S. EPA) has the authority and obligation to regulate carbon dioxide emissions from automobiles. Recently, the U.S. EPA has decided that carbon dioxide poses a threat to human health and the environment and that it will now be added to a list of 5 other greenhouse gases that can be regulated under the Clean Air Act. Given recent activity regarding carbon dioxide emission regulations, it is projected that the federal government may enact a carbon cap-and-trade bill. When this eventually occurs, utility companies and coal producers are in a position to be particularly affected by federal carbon dioxide regulation due to the large carbon dioxide footprint of coal-fired power plants. Although no carbon dioxide standards have been applied to power plant emissions in the U.S., plans for dozens of new coal-fired power plants have either been scrapped or delayed due to issues revolving around states concerned with future climate change legislation. Whether there is global consensus on the causes of climate change or not, it appears that carbon dioxide-emitting industries in the U.S. will soon be required to implement carbon management protocols that reduce emissions and (or) purchase or produce carbon credits.

The present invention seeks to aid the United States in the pursuit of Energy Security in an environmentally safe manner. An objective of the present invention may be to set the stage for achieving the vision of "Clean Coal" by turning carbon dioxide into a valued resource rather than a costly expense and long-term liability risk. In addition to coal, embodiments of the present invention have applications in carbon dioxide capture for fossil fuel conversion sources, natural gas-fired power plants and perhaps even distributed generation fuel cells, as well. Solving the carbon dioxide challenge for both coal and natural gas may assure the commercial viability of United States energy industries in a carbon constrained world and in turn may secure the Nation's economic prosperity.

Subsurface injection of carbon dioxide (also termed "geological carbon sequestration") has been considered as a default method for large-scale carbon sequestration, even though the associate costs of carbon dioxide isolation and purification from flue gas, compressing, transportation, and injection are prohibitive, and little is known about the long term sustainability and potential environmental impacts. Therefore technologies that can achieve source capture and sequestration of carbon dioxide is highly desired. Technically and economically, capture and conversion of carbon dioxide in proximity of emission sources, such as power plants, can offer the most cost-effective model of sustainable carbon sequestration.

Biological techniques as represented by microalgae reactors have been investigated since the 1970s and are now implemented at pilot scale for carbon dioxide capture and conversion to biomass. Although the algae-based technology shows potential in carbon dioxide capture, it may be limited by the light source (i.e. sunlight) for photosynthesis, the primary carbon dioxide-fixation pathway in algae. Another limitation may be the large area of land required to operate the photobioreactors. These obstacles, however, may be overcome by the bacterial reactor in the various embodiments of the present invention. Bacteria may be the best candidates in bio-trapping of carbon dioxide thanks to their high reproduction rate and ubiquitous distribution.

DISCLOSURE OF THE INVENTION

The present invention may provide biological carbon capture and conversion systems and methods to remove carbon dioxide from emissions. In embodiments, the present invention may integrate a carbon capture process into existing fuel combustion sources including combustion power plants and natural gas fueled fuel cell plants as a biological carbon capture and conversion system to remove carbon dioxide from emissions.

The resulting biomass produced may be reprocessed as fertilizer, feedstock, fuel, biofuel, or the like or may even be directly injected into the combustion facility (such as perhaps in co-fired applications). It is a goal of the present invention to utilize carbon dioxide as a value-added product of fossil-fuel power plants rather than a production-limiting waste product. In this way the carbon originally released from coal combustion can be captured and recycled in perhaps a closed-loop system, thus, significantly lowering overall carbon emissions and even improving plant efficiency.

It is another goal of the present invention, in embodiments, to enhance economic and energy security of the U.S. through the development of a technology that can reduce energy-related emissions of greenhouse gas and possibly improve the energy efficiency of power generation utilities and perhaps even to ensure that the U.S. can maintain a technological lead in this field. Additionally, this concept may support many goals of the Administration's Energy and Environment Agenda including investment in the next generation of energy technologies, producing more energy at home and promoting energy efficiency (perhaps through biofuel and co-fire applications for the biomass produced), closing the carbon loophole, and promoting U.S. competitiveness.

The impacts of embodiments of the present invention may provide utility companies with an environmentally responsible and economically viable carbon capture system. Furthermore, the utilization of this technology can be relatively rapid compared to other options for carbon capture such as geologic sequestration which may still require years of testing and modeling as well as sophisticated site characterization and large capital costs with each deployment to ensure injection activities do not create a legacy of potential liability for end users and future generations of Americans. In addition to the potential for a relatively rapid R&D phase, low risk to the end user in terms of long term liability, and the ability to improve plant efficiency through biofuel production and (or) co-fire applications, the biologic carbon capture system can almost certainly create new green jobs associated with the design, construction, maintenance and operation of these systems at power plants across the country as well as spur increased activity and innovation in the bio-processing/biofuel industries focused on utilizing the enormous quantities of biomass that can be produced.

Naturally, further objects, goals and embodiments of the inventions are disclosed throughout other areas of the specification and claims.

MODE(S) FOR CARRYING OUT THE INVENTION

Figure 1:
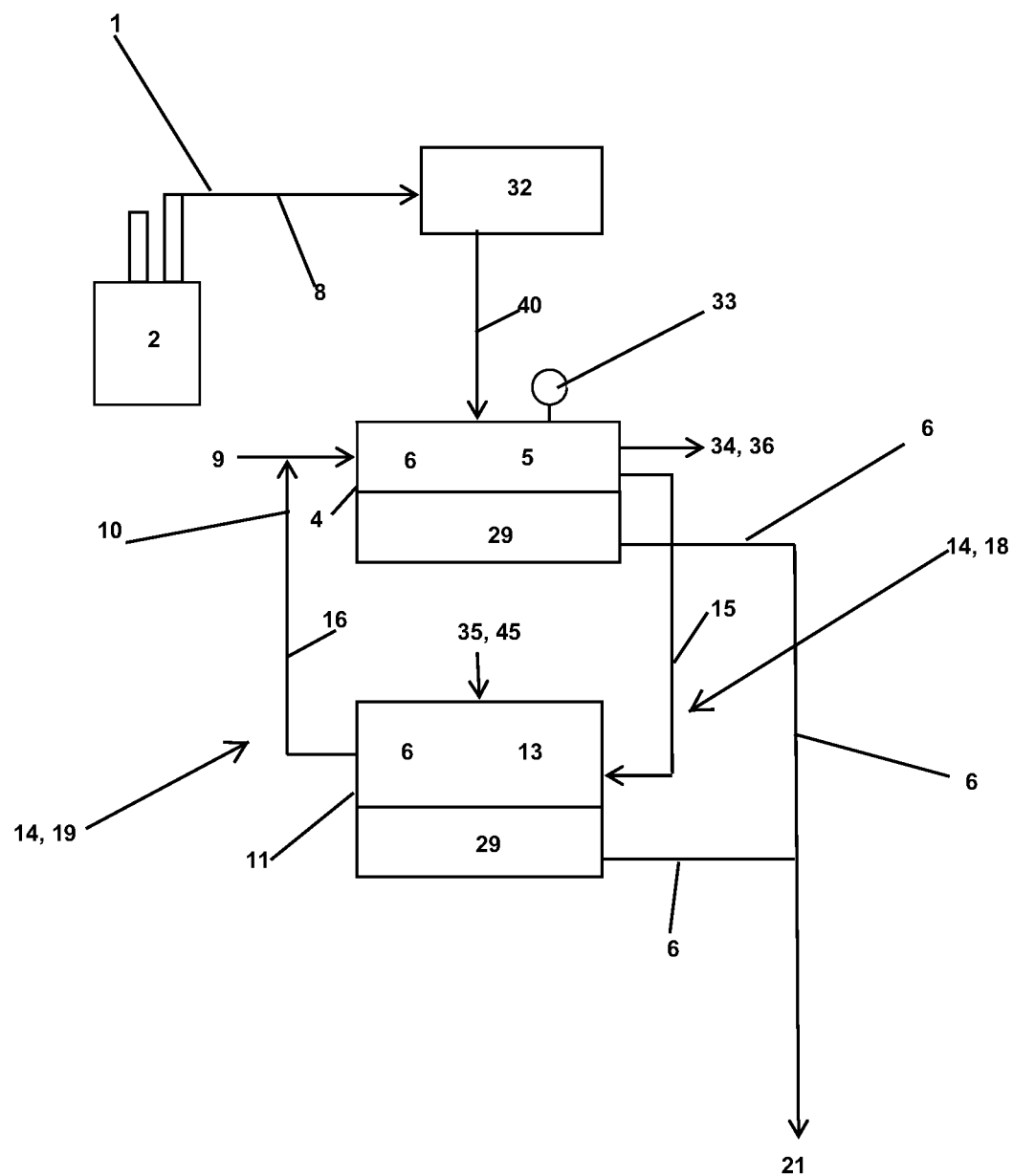
FIG. 1 shows a conceptual model of bacterial reactor system for carbon dioxide capture and conversion into biomass in accordance with some embodiments of the present invention.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

The present invention, may provide in various embodiments, methods of reducing carbon dioxide pollutants and perhaps even processing systems for reduction of carbon dioxide pollutants. For example, a method may include but is not limited to producing at least some carbon dioxide emissions from a carbon dioxide emittingsource; containing said at least some carbon dioxide emissions from said carbon dioxide emittingsource; efficiently introducing said at least some carbon dioxide emissions from said carbon dioxide emittingsource into at least one processing reactor; chemoautotrophically digesting carbon dioxide of said at least some carbon dioxide emissions with a plurality of chemoautotrophic bacteria in said at least one processing reactor; biologically producing at least some biomass from said chemoautotrophic digestion of said carbon dioxide with said chemoautotrophic bacteria; and perhaps even ecologically reducing atmospheric release of said carbon dioxide emitted from said carbon dioxide emitting source. A system may include but is not limited to a supply of at least some carbon dioxide emissions from a carbon dioxide emittingsource; an emissions container configured to contain at least some of said carbon dioxide emissions from said carbon dioxide emittingsource; at least one processing reactor configured to receive said at least some of said carbon dioxide emissions from said carbon dioxide emitting source; a plurality of chemoautotrophic bacteria in said at least one processing reactor configured to digest at least some of said carbon dioxide; an amount of biologically produced biomass by said chemoautotrophic bacteria located in said at least one processing reactor; and perhaps even an ecological reduction of atmospheric release of said carbon dioxide emissions.

Initial understanding of the present invention may begin with the fact that embodiments using chemoautotrophic bacteria perhaps even in a bioreactor for carbon dioxide consumption may be combined with various technologies such as but not limited to: fossil fuel consumption sources, power generation source, cement producing plants, coal refineries, oil refineries, refineries, lime producing plants, non-power generation sources, coal-fired power plants, natural gas-fired power plants, generation fuel cells, combustion power plants, or the like. Fossil fuel consumption sources may include any type of system or application in which a fossil fuel may be consumed or perhaps even converted in the process. For example, coal is heated in cement plants and power generation sources in the production of cement and energy and perhaps even crude oil may be converted into gasoline, diesel fuel, asphalt, or the like at refineries and the like. In embodiments, fossil fuel conversion sources may include any system or industrial system in which carbon dioxide is generated and emitted into the atmosphere.

Generally, chemoautotrophic bacteria, such as sulfur-oxidizing bacteria, may be a candidate species to fix carbon dioxide emitted from various processes. Chemoautotrophic bacteria may utilize elemental sulfur, various sulfide minerals, sulfur containing compounds, or other products as an energy source (e.g., electron donors) and carbon dioxide as their primary carbon source. Chemoautotrophic bacteria may efficiently oxidize sulfur containing compounds, sulfur and perhaps even sulfides, may fix carbon dioxide, and may even produce biomass or perhaps even high cell biomass as an end product. Chemoautotrophic bacteria (5) may be a carbon dioxide emissions scrubber in which they may be utilized to scrub carbon dioxide from emissions of fossil fuel consumption sources which may be considered a carbon dioxide capture technique for the purpose of meeting emission values imposed by cap and trade legislation or the like.

One example of a flow process representing various embodiments of the present invention is demonstrated in FIG. 1, where at least one processing reactor (4) may be configured to receive and even process emissions such as raw flue gas from stack emissions from a fossil fuel consumption source (2). A fossil fuel consumption source (2) may release emissions which may include a supply of carbon dioxide emissions (1) and other emissions (8) such as nitrogen, nitrogen oxide, sulfur oxide, oxygen, combinations thereof, or the like emissions. Carbon dioxide emissions may be efficiently introduced, perhaps even passing through a heat exchanger (32) for cooling of the emissions in some embodiments, into at least one processing reactor (4). Efficient introduction may include filtering, channeling, flowing, directing, capturing, moving, transporting, connecting (either directly or indirectly) and the like of emissions from a fossil fuel consumption source to at least one processing reactor. A plurality of chemoautotrophic bacteria (5) may be included in at least one processing reactor to which the plurality of chemoautotrophic bacteria (5) may be configured to chemoautotrophically digest carbon dioxide from the emissions. Chemoautotrophic bacteria may include a plurality of bacteria of the same species or may even include a plurality of bacteria from more than one species of bacteria and may be carbon fixing bacteria and sulfur oxidizing bacteria, such as but not limited to *A. ferrooxidans, Sulfolobus* spp., and combinations thereof. These biologically based carbon dioxide capture technologies may utilize natural occurring reactions of carbon dioxide within living organisms like chemoautotrophic bacteria. Carbon dioxide from emissions may be enzymatically transformed and integrated into the bacteria, thus carbon may be stored in the cell biomass. The biologically produced endproduct biomass (6) may be dominantly amino acids, carbohydrates, and water. It is noted that the chemoautotrophic bacteria may be utilized in various carbon dioxide capture technologies with or without a processing reactor and the chemoautotrophic bacteria may be supplied from any kind of source for use in these systems. In embodiments, a processing reactor may include any type of vessel, reactor, container, system, or the like.

An amount of biologically produced biomass (6) may be collected from at least one processing reactor with a biomass collector (29). In embodiments, a biomass collector (29) may include a continuous biomass removal element for continually removing biomass from at least one processing reactor such as but not limited to a concentrator, centrifuge, disk-stack centrifuge, or the like. The produced biomass may be readily collected and removed from the reactor to allow recycling of the medium. Biomass (6) may be processed or even converted into a product (21) which may include but is not limited to methane, hydrogen, alcohol, fertilizer, feedstock, bioenergy, food, biofuel, biodiesel, military fuels, ethanol, plastics, animal feed, food amendments, or the like; therefore, perhaps a sellable end-product which can off-set operational expenses or even generate surplus profit. The process may be cost-effective in capturing carbon dioxide from emissions, let alone the side benefit from the biomass end product. The commercial value of this technology, perhaps when used in scaled up operations, could be unlimited.

A variable amount of biomass can be produced through this process depending on the level of carbon sequestration required by the emissions source; however, even modest amounts of carbon capture and conversion may result in the production of massive amounts of biomass. The ability of the Nation to become self-sufficient with sustainable energy technologies is an essential aspect for achieving energy security and, in turn, economic security and prosperity. Our consumption rate of domestic coal may be slowed by feeding the biomass into the plant as a fuel along with perhaps a smaller amount of coal. This may lengthen the duration that our domestic coal can be used to achieve energy security. Utilizing the biomass to produce transportation fuels may enable lessening import of foreign oil from Venezuela and the Middle East.

As mentioned above, the present invention may provide an energy supply (9) perhaps even a chemoautotrophic bacteria energy supply to a plurality of chemoautotrophic bacteria (5) which may be located in at least one processing reactor (4). The energy supply (9) needed to drive biological carbon fixation to the chemoautotrophic bacteria in this type of reactor can be added, for example, as a supply of sulfur containing compounds (16) such as metal sulfides, hydrogen sulfide ($H_2S$) or perhaps even elemental sulfur, of which there may be large stockpiles worldwide as this is a waste product of the oil refining process. Additionally, it may be possible to recycle an energy supply to the chemoautotrophic bacteria with a recycled chemoautotrophic bacteria energy supply (10) within a system and perhaps even from a second processing reactor (11) which may generate the chemoautotrophic bacteria energy supply. In some embodiments, a recycled chemoautotrophic bacteria energy supply may be recycled from within the same processing reactor. A processing reactor, or in some instances a second processing reactor (11), may include sulfate reducing bacteria which could reduce sulfate generated by the chemoautotrophic bacteria to sulfides to which the sulfides can then be utilized by and even recycled to the chemoautotrophic bacteria as their energy supply. Sulfate reducing bacteria ("SRB") may be a sulfur or even a sulfate reducing bacteria and may even include any bacteria that can reduce oxidized sulfur species. Thus, in embodiments, a second processing reactor (11) may produce a supply of sulfur containing compounds (16) and may even be a sulfate-reducing processing reactor. A supply of sulfur containing compounds (16) may include elemental sulfur, sulfides, metal sulfides, hydrogen sulfide, or the like which can be consumed by chemoautotrophic bacteria. Further, the sulfate-reducing bacteria may also produce biomass (6) which may be collected and processed as discussed herein.

Accordingly, in embodiments, recycling of an energy supply, for example sulfur containing compounds, to the chemoautotrophic bacteria may include providing sulfate reducing bacteria (13) in a second processing reactor (11), connecting (either directly or indirectly) at least one processing reactor (4) containing the plurality of chemoautotrophic bacteria to the second processing reactor (11) containing the sulfate reducing bacteria with perhaps a connection (14), generating sulfate or other oxidized sulfur species (15) in the least one processing reactor (4) containing the chemoautotrophic bacteria (5), supplying sulfate or oxidized sulfur (18) from the at least one reactor (4) containing the chemoautotrophic bacteria to the second processing reactor (11) containing the sulfate reducing bacteria (13), generating sulfur containing compounds (16) in the second processing reactor (11) containing the sulfate reducing bacteria (13); and perhaps even supplying sulfur containing compounds (19) from the second processing reactor (11) containing the sulfate reducing bacteria (13) to the at least one processing reactor (4) with the plurality of chemoautotrophic bacteria (5) as may be understood from FIG. 1. In this embodiment, the at least one processing reactor (4) may be configured to generate sulfate or oxidized sulfur (15) (perhaps by the chemoautotrophic bacteria) and the second processing reactor (11) may be configured to generate sulfur containing compounds or reduced sulfur (16) (perhaps by the sulfate reducing bacteria) and the two reactors may be connected (14) (either directly or indirectly) so that the sulfate and sulfur, or even the oxidized and reduced sulfur, can be supplied each other. The two reactors may be physically apart from each other, may be connected or even joined by a permeable membrane or the like as may be understood in FIG. 2, or even any type of connection or attachment including but not limited to tubes, flows, pipes, or the like. In other embodiments the contents of the two reactors may be combined into one reactor and perhaps even multiple processing reactors may be used.

Alternatively, a sulfate reducing bacteria energy supply (35) may be provided to the sulfate reducing bacteria (13) which may include waste organic carbon, organic matter, recycled organic matter such as cell mass or other residual materials collected from the biomass or byproducts of the sulfate reducing bacteria and recycled back to the sulfate reducing bacteria, combinations thereof or the like. The sulfate reducing bacteria energy supply (35) may be recycled within a system or may even be supplied from an outside source. In this case, the energy input to drive the sulfate reducing processing reactor could be in the form of waste organic carbon sources including but not limited to waste dairy products, returned milk, waste dairy byproducts, cheese whey, straw, woodchips, or the like. In other embodiments, a recycled process biomass residue electron donor supply (45) may be supplied to the sulfate reducing bacteria such that recycled process biomass residue may be used by the sulfate reducing bacteria as an electron donor supply.

Figure 2:
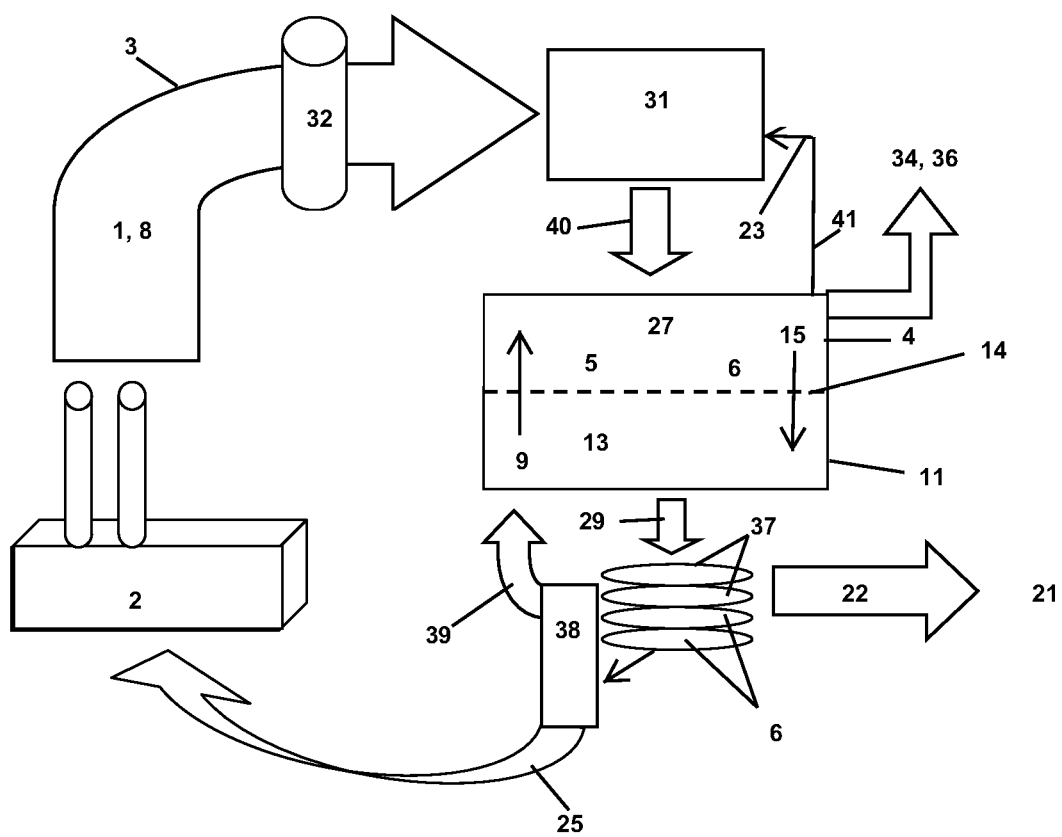
FIG. 2 shows a conceptual model of an overall biological carbon capture and conversion process in accordance with some embodiments of the present invention.

In embodiments and as can be understood from FIG. 2, emissions from a fossil fuel consumption source including carbon dioxide emissions (1) and perhaps even other emissions (8) as discussed herein may be contained as they exit the fossil fuel consumption source (2) perhaps even in an emissions container (3). An emissions container (3) may prevent up to about 100% of the emissions, in particular carbon dioxide emissions, from entering the atmosphere and may transport the emissions to at least one processing reactor (4). In other embodiments, a system may prevent up to about 65%, up to about 70%, up to about 75%, up to about 80%, up to about 85%, up to about 90%, up to about 95%, up to about 99%, and perhaps even between about 65% to about 100% of carbon dioxide emissions from entering the atmosphere. An emissions container may be a receptacle, filter, channel, pipe, enclosure, or the like. In embodiments, emissions may be processed prior to being introduced into the at least one processing reactor. An emission pretreatment element (31) may pretreat the emissions perhaps even minimally to separate carbon dioxide from the other emissions. In this respect, an emission pretreatment element (31) may be a carbon dioxide emission separator. After emissions may be treated in the emission pretreatment element (31), carbon dioxide may be sent (40) to at least one processing reactor (4) for carbon digestion as discussed herein.

A processing reactor (4) may contain a growth medium (27) which may include but is not limited to bacteria, mineral salts, trace vitamins, enzymes, a commercially available enzyme for pH control, pH control (33), or the like. The growth medium (27) may have adequate retention for carbon dioxide thus providing a carbon dioxide retainer but other gases such as nitrogen may flow through with perhaps no solubility. Bacteria such as chemoautotrophic bacteria in the processing reactor may digest carbon dioxide at a digestion rate which is up to or even equal to a carbon dioxide inflow rate into the processing reactor. This may provide for optimal operation.

As biomass (6) may be removed and collected from at least one processing reactor (4) and perhaps even from a second processing reactor (11) into a biomass collector (29) it may contain both biomass (6) and water (37). Water (37) may be returned (39) back to the processing reactor(s) or otherwise recycled into a system. These may be separated out with a separator (38) and may even be dried in a biomass dryer (22) to which the biomass may be further processed into various products (21) as discussed herein. In embodiments, the biomass may be injected or even fed back into a fossil fuel consumption source with perhaps a fossil fuel consumption source system injector (25) perhaps as fuel for the consumption source.

Embodiments of the present invention may also potentially extend the supply of non-renewable fuel sources such as coal or the like. Biomass produced in the processing reactor(s) may be processed into biofuel such as biodiesel or perhaps even ethanol or can be co-fired with coal in the power plant, then the carbon dioxide initially liberated from coal through combustion can be captured and re-combusted. This process can potentially recycle the carbon dioxide several times, and thereby reduce the amount of non-renewable fuel required to meet a plant's energy production goals. Further, any undigested carbon dioxide (41) remaining in the processing reactor (4) may be recycled. For example, an undigested carbon dioxide recycling element (23) may recycle unprocessed carbon dioxide (41) back into a system perhaps even back into the fossil fuel emissions or even into an emission pretreatment element (31) as can be understood from FIG. 2. A processing reactor may discharge other gases such as nitrogen (34) and oxygen (36) from the reactor and release them into the atmosphere or otherwise release these byproducts. In embodiments, waste products, impurities, contaminants or the like may be removed from the processing reactors or system as well.

Embodiments of the present invention may achieve the vision of "Clean Coal" by turning carbon dioxide into a value-added product of coal-fired power plants, as well as other fossil fuel based consumption systems, rather than a production-limiting waste product that needs to be disposed of through costly processes (e.g., deep subsurface injection/sequestration). As can be understood from the discussion above, one concept of the system may include flue-gas injection, which may provide $CO_2$ from flue-gas, into an aqueous reactor where chemoautotrophic bacteria such as carbon-fixing bacteria may pull carbon out of solution and may incorporate it into their biological tissues and lipids (e.g., carbon fixation), perhaps effectively capturing the carbon dioxide and converting it into biomass that can be continually harvested from the processing reactor. This biomass can potentially be reprocessed as fertilizer, feedstock, biofuel, or perhaps even directly injected into a combustion facility (e.g., co-fired applications) to offset the amount of coal needed to achieve the plant's Btu goals and, therefore, perhaps dilute other impurities in the flue gas such as $NO_x$ and $SO_x$ stemming from coal combustion. In this way the carbon originally released from coal combustion can be captured and may even be recycled in a closed-loop system, perhaps, significantly lowering overall net carbon dioxide generation and emissions perhaps allowing a plant to maintain power production without exceeding allowable carbon dioxide limits. Embodiments of the present invention may elucidate optimal conditions that maximize carbon assimilation rates of chemoautotrophic bacteria in a bacterial system which may include a two-part bacterial system as illustrated in FIGS. 1 and 2

There are many advantages to utilizing non-photosynthetic organisms, such as chemoautotrophic bacteria, for carbon capture including the ability to operate in various parameters such as but not limited to all latitudes and climates, 24 hours a day, and perhaps even in densely populated reactor tanks rather than operating only when and where adequate sunlight may be available in ponds or transparent tubes that may require large amounts of surface area to achieve sufficient illumination for photosynthesis, temperature control systems, and even supplemental lighting for 24-h operation. The need for adding heat during the winter season in northern climates may be avoided with non-photosynthetic organisms and the additional controls and design of algae-based systems may also add significant capital and maintenance costs that can be significantly reduced in a simple chemoautotrophic bacterial growth tank that can be located underground to help eliminate exposure to the elements as well as reducing the overall process footprint on site. Therefore, in embodiments, a processing reactor may be operated in any climate, up to 24 hours a day, and may even contain a dense population of chemoautotrophic bacteria.

In embodiments, optimal conditions (e.g., pressure, temperature, and pH), nutrient concentrations (if any), sulfur concentrations, sulfur species concentration, inorganic carbon concentrations (e.g., $CO_2$, $HCO_3^-$, or $CO_3^{2-}$ depending on pH), inorganic ion concentrations, bacterial cell densities, and the like can be determined for maximum carbon fixation rates of various species/strains of carbon fixing bacteria. Inorganic carbon may be introduced as pure carbon dioxide for preliminary tests and then in simulated flue gas mixtures for more sophisticated tests that may also determine the lowest level of flue gas purity (i.e., least amount of pretreatment required and largest cost savings) for efficient bacterial growth and subsequent carbon capture. As discussed above, the reactor may also be equipped with a disk-stack centrifuge or similar device capable of continually removing biomass from the reactor at pre-determined cell densities to produce a bacterial paste that can be used for determining the quality of the biomass and potential applications such as biofuel production or use as a co-fired fuel for blending with coal.

Alternative embodiments of the present invention may include a multistep biological and chemical process for the capture and conversion of carbon dioxide and/or other sources of inorganic carbon, into organic compounds, where one or more steps in the process utilize obligate and/or facultative chemoautotrophic microorganisms, and/or cell extracts containing enzymes from chemoautotrophic microorganisms, to fix carbon dioxide or inorganic carbon into organic compounds where carbon dioxide gas alone or in a mixture or solution as dissolved carbon dioxide, carbonate ion, or bicarbonate ion including aqueous solutions such as sea water, or in a solid phase including but not limited to a carbonate mineral, is introduced into an environment suitable for maintaining chemoautotrophic organisms and/or chemoautotroph cell extracts, which fix the inorganic carbon into organic compounds, with the chemosynthetic carbon fixing reaction being driven by chemical and/or electrochemical energy provided by electron donors and electron acceptors that have been generated chemically or electrochemically or input from inorganic sources or waste sources that are made accessible through the process to the chemoautotrophic microorganisms in the chemosynthetic reaction step or steps.

EXHIBIT A

Background of Alternative Embodiments of the Invention

The present invention may include a Chemoautotrophic ("CAT") bacteria-based $CO_2$ consuming process for the production of biodiesel and other bio-based products. The CAT process can provide the energy sector and industrial emitters with a carbon capture and conversion technology that may produce salable products perhaps thereby turning an environmental hazard and expense (such as a greenhouse gas "GHG") into a valued resource with the potential to significantly reduce or perhaps even eliminate all foreign oil imports. If all power plant $CO_2$ emissions are converted to biodiesel such as perhaps to about 64 billion barrels of biodiesel, then the domestic transportation fuel market could be well supplied providing the U.S. with a strong export product creating a double benefit for the U.S. trade deficit. Power plant efficiency can improve and the cost of electricity ("COE") impact to Americans may be well below the ARPA-E target of less than a 20% increase.

Summary of Alternative Embodiments of the Invention

A variety of bacteria can be developed and evaluated for $CO_2$ consumption and the biomass precursor quality from which bio-oils may be extracted and end products produced. A two bioreactor system may be advanced to facilitate reduction of $SO_4^{2-}$ to $H_2S$ using sulfur-reducing bacteria ("SRB"). $H_2S$ may supply an energy source to the CAT bioreactor. The $SO_4^{2-}$ produced in the CAT bioreactor may be recycled to generate additional $H_2S$ in a first bioreactor. Non-extractable fractions may be converted to nutrients to drive the bacterial system and perhaps even supply essentially all of the nutrient needs. Biomass generated in both the CAT and SRB bioreactors can be processed to obtain purified lipids and other substances for processing into biodiesel, bioproducts, and other materials. Experiments may elucidate data needed to design and establish operational parameter performance and control values for a bioreactor. The bio-oils may be used as a precursor to synthesize bioproducts and petroleum replacement products.

Modeling and systems integration can be conducted for large-scale power plant applications and perhaps even small-scale operations such as cement and fertilizer manufacturing facilities as a "drop in" process into a conventional biodiesel plant and may even impact of different amounts of carbon capture on power plant efficiency and costs. An important aspect of the deployment project may entail assessing market penetration for CAT biodiesel and other end products. Bio-oils can spur several domestic industries—a number of transportation fuels and other chemicals and polymers needed to sustain domestic U.S. industries and infrastructure assets, such as highways, airport runways, or the like. This may be a dramatically different approach compared to coal gasification for domestic production of such end products. The proposed concept may represent a transformational pathway to convert $CO_2$ into petroleum replacement products such as biodiesel and may even provide an efficient and economical method of capturing $CO_2$.

Naturally, further objects, goals and embodiments of the inventions are disclosed throughout other areas of the specification claims.

DETAILED DESCRIPTION OF ALTERNATIVE EMBODIMENTS OF THE INVENTION

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may investigate carbon assimilation rates of chemoautotroph bacteria such as sulfur oxidizing bacteria (bacteria that fix inorganic carbon ($CO_2$) through the oxidation of chemicals rather than from sunlight). This process may use these organisms in a biological carbon capture and conversion system to remove carbon dioxide ($CO_2$) from utility and industrial facility emissions.

The proposed approach may rely on the concept that synthetic symbiosis between sulfur reducing bacteria and sulfur oxidizing bacteria can be sustained in a controlled manner with perhaps predictable biomass production rates in a specified operating regime. Furthermore, this may be accomplished through chemical looping of sulfur between sulfur reducing heterotrophs and sulfur oxidizing chemolithioautotrophs. In addition, the technical approach may lend itself to tailoring of the operational conditions for the harvesting of biological lipids and fatty acids perhaps for the purpose of producing biofuels and other petroleum replacement products. Also, the harvested materials may display unique attributes, in that bacteria may produce a wide range of high-valued bioproducts such as paraffin class hydrocarbons, as well as perhaps even standard biodiesel precursor lipids. The non-extractable biomass residue may be used as the nutrient source for the sulfur-reducing bacteria. The concept herein may address the deficiencies of the state of the art by producing a system that may not be reliant on an uncontrolled source of energy for the conversion of $CO_2$ into biofuels, perhaps even while providing a low-cost carbon capture technology for GHG emitting facilities.

Embodiments of the present invention may address specific societal goals in that it (1) may enhance economic and energy security of the U.S. through the development of a technology that could produce energy-dense, infrastructure compatible liquid fuels from $CO_2$ perhaps as the only carbon source thereby reducing petroleum imports (2) may effectively capture stationary sources of energy-related emissions of greenhouse gases (GHG), (3) may improve the energy efficiency of GHG emitting facilities, such as power generation utilities and industrial and manufacturing facilities, and perhaps even (4) may ensure that the U.S. could maintain a technological lead in this field. Additionally, the concept may support many of the goals of the US administration including investment in the next generation of energy technologies, producing more energy at home and promoting energy efficiency (by producing biofuels and bioproducts that store carbon), and perhaps even promoting U.S. competitiveness. As such, the technology can bring about a transformation of the industry, providing a leap in advancement to overcome a number of obstacles that are currently limiting the deployment of biofuels and carbon capture for retrofitting utility and industrial GHG facilities for GHG emissions control.

Embodiments of the present invention may include $CO_2$ removed from a flue gas and injection into an aqueous reactor where carbon-fixing bacteria may use carbon and incorporate it into their biological tissues and lipids. The process may capture $CO_2$ using chemoautotrophic bacteria in an anaerobic bioreactor, which may be fueled by $H_2S$ supplied by perhaps a separate bioreactor occupied by perhaps sulfate reducing bacteria ("SRB"). The $SO_4^{2-}$ generated as a product of sulfide oxidation in the CAT bioreactor may be used as a source of electron acceptors for making sulfides (electron donors) in the anaerobic system. The biomass may be harvested from the bioreactor and processed into biofuel and/or petroleum replacement products. The residual biomass from the oil extraction may be used as the nutrient source for the process. Oil yields may be estimated to be sufficient to provide residual biomass to meet the nutrient needs of the process.

Biofuels may be currently one of the few commercial alternatives to continued dependency on oil. The Energy Independence and Security Act of 2007 (EISA) established a goal of 36 billion gallons of biofuels by 2022 to power our cars, trucks, jets, ships, mining equipment, locomotives and tractors. Today only 12 billion gallons of biofuels are produced annually. The EIA's reference case for the 2010 Annual Outlook projects that most of the growth in liquid fuel supply will be met by biofuels—yet EIA also projects that the industry will not meet the 2022 goal. The existing biofuels industry represents three generations of fuels that in their own right were transformational and market disruptive.

The first-generation agricultural-based ethanol biofuels industry has grown from 1% of the U.S. fuel supply to 7% in 2008. However, the Renewable Fuel Standard in the EISA has effectively placed a 15 billion gallon cap on ethanol production from corn as part of the new 36 billion gallon target for 2022. The remainder of the target has to be met with second and third generation advanced biofuels, including cellulosic ethanol, biobutanol, biobased diesel, and other biofuels that are a direct replacement for petroleum-based fuels.

While corn ethanol has played a key role in establishing the U.S. biofuel industry, it remains controversial, due in part to the fact that using corn for biofuels displaces crops that would otherwise have been used for humans, requires high water use, and requires high amounts of land. Recent estimates are that corn based ethanol has replaced 32% of the corn crop in the U.S. for ethanol production.

While cellulosic ethanol may hold great promise, the lack of commercial-scale facilities in test or in operation has created a degree of uncertainty regarding the true operating expenses required for producing cellulosic ethanol. While cellulosic ethanol is transformational over corn based ethanol, unmodified engines may be unable to process volumetric blends above 10% ethanol without significant damage. Although Flex Fuel Vehicles (FFVs) enable the driver to choose between using gasoline or ethanol blends up to 85% (E85), market acceptance in the U.S. is very low, since only 1% of U.S. gas stations offer E85 ethanol pumps.

The third-generation of biofuels, based on algae may allow for the production of 'drop-in fuels' while also making use of the pre-existing petroleum infrastructure. As such, algae may secrete lipids with chemical compositions similar to petroleum-based hydrocarbons. Algae-based fuels may have growth pattern and harvesting processes qualitatively different from any other alcohol- or oil-producing biomass. Algae, due to their high oil yield (up to about 50× the amount of biofuel compared to other leading feedstocks), uptake and cycling of $CO_2$, and perhaps even capacity to be grown on marginal land in brackish and/or saline water may have spurred its development. Algae may have yields of about 2,000 gallons per acre per year in open ponds and yields may be increased up to about 10,000 gallons per acre per year, depending upon the genetically modified organisms ("GMO") strains that are used and perhaps even the utilization of photobioreactors (PBRs). However, those strains that produce high yields may also tend to have slower growth rates, thereby creating even higher land burdens for production.

The proposed chemoautotrophic-based technologies may be the fourth generation biofuel with perhaps equivalent transformational and market disruption attributes that the third generation algae-based biofuels industry had over the first and second generation ethanol biofuels. Like third-generation biofuels, the bacteria-based technologies may allow for 'drop in' fuels that replace and are compatible with petroleum-based fuels, not solely as an additive. Although CAT based systems may not produce a very high lipid content, they may have unique compositions that may allow for other very high valued other products such as essential equivalent lipid yields with bacteria as with algae.

Due to the fact that CAT based systems do not need sunlight for growth, the land area required for the CAT bacteria growth may be about $1/50^{th}$ the size needed for open algae-based production and may be about $1/10^{th}$ the size for algae in photobioreactors that need expensive energy-consuming artificial lighting. Fourth-generation bio-fuels, due to their smaller footprint, may be more amenable to be co-located with small local and large $CO_2$ sources, such as power plants.

Biofuels production may not be the only benefit of bacteria-based systems. Emerging bacteria-based biofuels production processes may also be carbon capture technologies. According to the EIA, the United States energy industry emitted over 5.9 billion metric tonnes of $CO_2$ in 2006 and is projected to emit over 6.4 billion metric tonnes/yr by 2030, an 8% increase in emissions. Those fuels with the largest emissions are coal and oil, with 2.5 and 2.6 billion metric tonnes/year, respectively. As a result of climate change debate, the U.S. is considering mandatory reductions in $CO_2$ in incremental stages, as such 5% additional reduction of $CO_2$ per every 5 years in order to qualify for credits.

Carbon capture and storage (CSS) technologies may be expensive and may consume large amounts of parasitic power. The high parasitic power load with CCS decreases plant net efficiency from perhaps about 36.8% to only about 24.9%, perhaps resulting in increased $CO_2$ emissions if power is purchased to offset the parasitic power. It is important to note that every about 1% of net plant efficiency decrease releases another about 20 million tons of $CO_2$ emissions fleet-wide annually. The high capital of CCS and the parasitic load may result in an increase in cost of electricity (COE) of between about 70 and about 80% with rates increasing from about 6.4 cents/kWh to about 11.4 cents/kWh.

The value to the power plant of an alternate CCS technology such as bacteria-based capture which may not significantly increase parasitic power can be calculated from these COE increases. For example, the total value to the utility of about 65% carbon capture on the about 550 MWe plant may result in about 10.4 cents/kWh, based on interpolated DOE's data between zero and about 90% percent capture. Assuming values of about 8000 hrs of annual plant operation and about 550 MWe net electric output, the total additional cost that would be incurred to meet about 65% CCS is estimated to be about $176 million annually. Clearly, the implementation of the proposed CAT bacteria biofuels process could significantly reduce the economic burden of carbon capture on the utility and the ratepayers, but also on the economics of the biofuels produced, enhancing energy and environmental security.

There may be an ongoing development in the area of bacteria-based biofuels. Although most bacteria generate complex lipid for specified chemical production, it has been reported that some bacteria can accumulate oils under some special conditions. Development of bacteria based biofuels and other energy related technologies have started to gain momentum in industrial applications. Some applications may include supplementing algae systems during non peak sunlight conditions to perhaps increase production. Other trends in the field include Amery's focus on utilizing bacteria as a micro-refinery by feeding the bacteria sugar cane and then 'milking the microbe' to secrete synthetic diesel. The microbe (e.g., algae, bacteria and the like) may be a mini-processor of biomass feedstock directly into fuels. Other companies may appear to have engineered both yeast and *E. coli* bacteria to make use of previously undiscovered metabolic pathways to convert sugars into hydrocarbon products than can be put straight into your gas tank, or perhaps even sent off to a refinery for processing. This may be nearly carbon neutral and may be about 65 percent less energy intensive than ethanol fermentation. The utility industry may have studied bacteria for waste treatment; one successful application is THIOPAQ® technology owned by a Netherlands company, Paques. This technology may have been adapted for sulfur removal from utilities. Chen has demonstrated that methane production may be possible from reverse microbial fuel cell. In this application, the nutrient source may typically be acetate and a voltage may be applied across the cell to increase and/or perhaps stimulate the oxidation of the nutrient source. Embodiments of the present invention may be totally different from these technologies due to its use of sulfur-based shuttle. Dual bacteria species may be used, the conversion of residue to supply the nutrients needed, (as opposed to use of external waste streams as the nutrient source) and the production of biodiesel and other bioproducts are examples of the process differences.

Embodiments of the present invention may include a CAT bacteria biofuels process which may be based on the synthetic symbiosis of bacteria by creating an energy shuttle through the use of sulfur recycling, which may represent a transformational step to the biofuels industry. Biofuels can be produced from $CO_2$ sources using chemoautotrophic (CAT) bacteria such as *Thiobacillus* ssp. and sulfur reducing bacteria (SRB) such as *Desulfovibrio desulfuricans* to form biomass that can be converted to biofuels.

Figure 3:
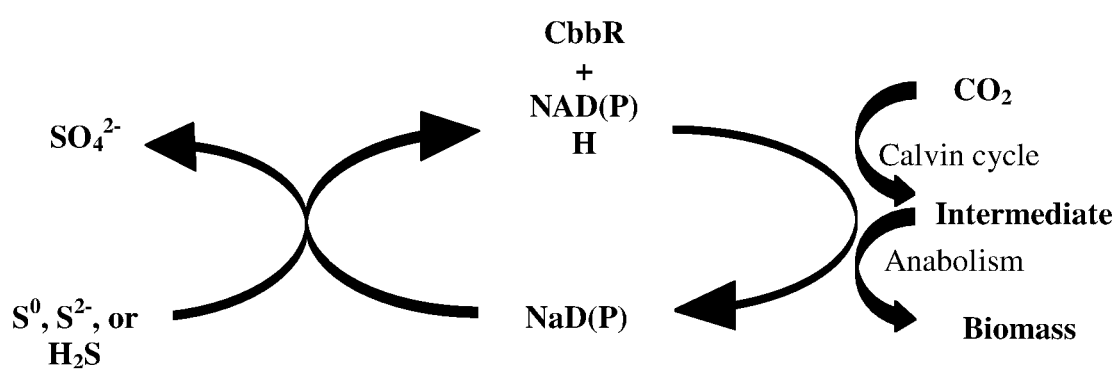
FIG. 3 is an example of a schematic summary of a chemoautotrophic $CO_2$ capture Calvin Cycle in accordance with embodiments of the present invention.

The microbial processes employed may be derived from two specific categories, sulfur reducing bacteria (SRB) and sulfur oxidizing bacteria (SOB). Sulfur reducing bacteria may use sulfate or sulfite to oxidize organic material for biomass generation, and release sulfides or elemental sulfur. Sulfur oxidizing bacteria (for example, lithotrophs) consume sulfides in combination with inorganic carbon such as $CO_2$ to produce biomass and may release sulfates. This process may be represented by the Calvin cycle and one variant may be depicted in FIG. 3. Sulfide may be a known biologic poison, and removal of the sulfide may stimulate growth of the sulfur reducing bacteria and perhaps even the transport of sulfides to the chemolithoautotrophs may supply them with the needed sulfur for their metabolism. In return the chemolithotrophs may oxidize the sulfide to sulfate or sulfite and it is returned to the SRB by recycle. Resulting biomass from both bacterial subsystems may be recovered using standard separation methods and may be processed as sources of lipids and paraffin for the production of petroleum replacement bio-products. The biomass residue present after lipid extraction may be used as a nutrient source for the SRB bioreactor.

Figure 4:
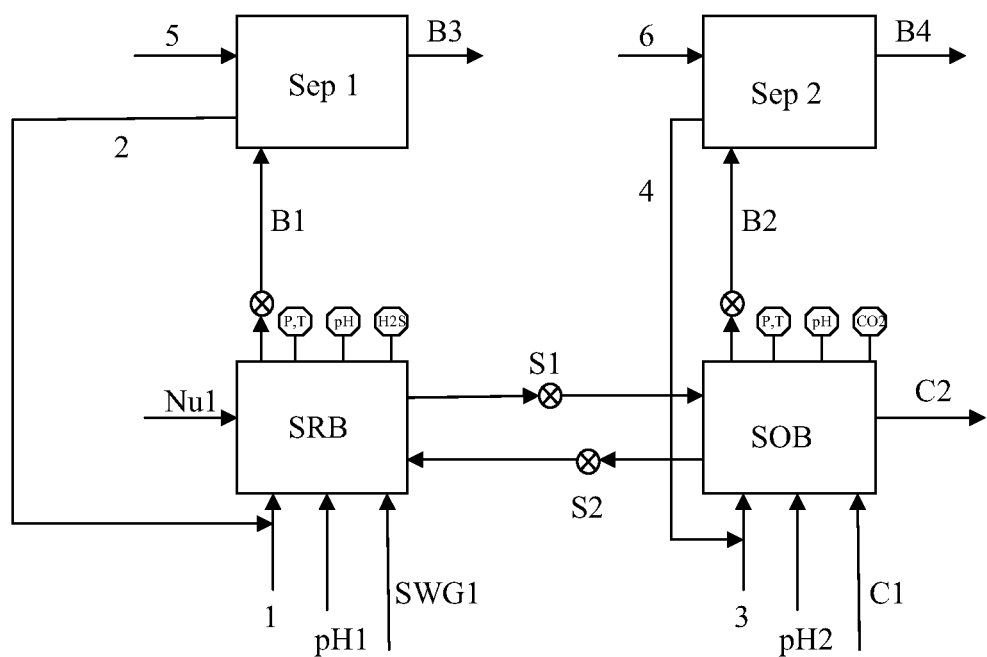
FIG. 4 is an example of a conceptual model of the CAT biological carbon capture and bioproducts process in accordance with embodiments of the present invention.

One embodiment of a conceptual model of the process is provided in FIG. 4. Nutrients delivered to the system at Nu1 may provide metabolic carbon to the SRB reactor bacteria. SRB reactor bacteria may convert sulfates and sulfites into $H_2S$ which may be removed from the reactor through S1. To further enhance the removal of $H_2S$ from the SRB reactor, nitrogen or low oxygen flue gas can be sparged through inlet SWG1. The sulfide rich gas stream may enter the SOB reactor from S1 and may be combined with $CO_2$ sparged from inlet C1. The $CO_2$ may be metabolically fixed in the bacteria of the SOB reactor and low $CO_2$ concentration flue gas may be removed from the system via outlet C2. During the process of fixing carbon in the SOB reactor, $H_2S$ may be converted to $H_2SO_4$ and other sulfates and sulfites. These highly soluble sulfur species may then be returned to the SRB reactor in a recycle loop S2. Each reaction vessel may be monitored for pH and additions of buffering solutions may be added to each reactor through pH1 and pH2, respectively. As biomass may accumulate in the given reactors there can come a time when critical mass has been achieved and the biomass may be ready for harvesting. Harvesting may be accomplished by removal of the biomass laden broth through B1 and B2 for each reactor respectively and delivering it to the associated biomass separators. Make up wash water may be delivered to each reactor through inlets 1 and 3. The biomass separators may be the first level biomass stream condensing stage in which the bulk broth may be removed and recycled through return streams 2 and 4 for each reactor subsystem. Depending on the separation technique employed, chemical addition such as flocculants and surfactants can be added through inlet streams 5 and 6.

Figure 5:
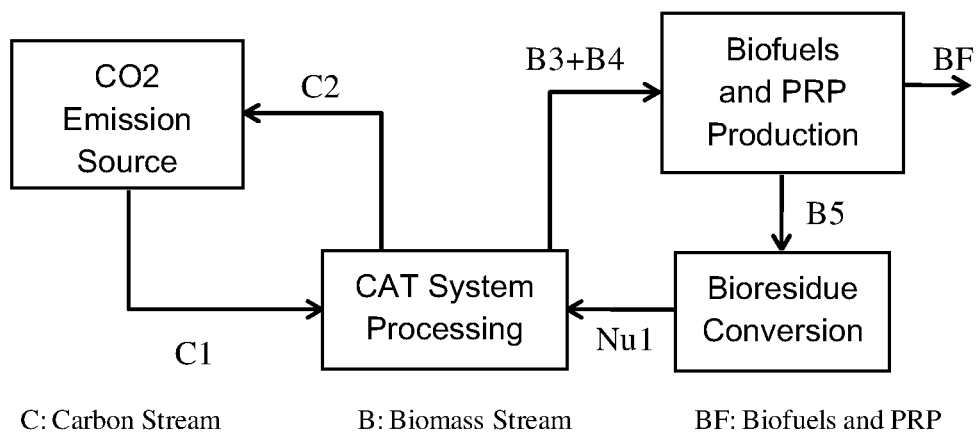
FIG. 5 is an example of an integrated $CO_2$ Capture, CAT and Bioproducts system diagram in accordance with embodiments of the present invention.

Condensed biomass streams B3 and B4 may then be transported to lipid and perhaps even oil extraction equipment perhaps either as individual stream or as combined streams. The CAT system can be dropped into a biofuels production loop as presented in FIG. 5.

$CO_2$ rich gas may leave the emissions source through flow C1 and may be supplied to the SOB reactor of the CAT system. Gas cleanup units may be inserted in the C1 and C2 flow, and then $CO_2$ lean gas may be returned to the emissions source for venting through a stack or even reused in the system elsewhere. Condensed biomass streams may be delivered to the biofuels and petroleum replacement products (PRP) production unit or may be delivered to a combination of units as perhaps either separate or combined streams through B1. B2 may convey the bioresidue left over after lipids and oil extraction to a bioresidue conversion process, where the residue may be broken down into a more readily metabolized nutrient source for microbial activity. Then the converted biomass may be fed back to the CAT system as nutrients for the SRB reactor. Biofuels and other PRP may then exit the system to be transported to end use nodes. Water treatment by-products produced during harvesting could be land-filled.

The products extracted from the SRB-CAT bacterial biomass may provide advantages for processing biofuels. Materials extracted from the biomass may contain lipids and paraffin. A study conducted by Davis (1968) indicated that the SRB *Desulfovibrio desulfuricans* contained 5 to 9% lipids with 25% of the lipids consisting of paraffin. Paraffin may be a high-valued component used for industrial purposes including synthesis of ozone inhibitors in rubbers and hot climate asphalt additives. The expected lipid content of CAT bacteria may be in the range of between about 20 to about 30%. The existence of paraffin in biomass generated by the CAT bacteria may be a unique part of the CAT biofuels and bioproduct process. If successful, the concept may leapfrog over today's ethanol and algae approaches perhaps due to its siting flexibility as well as accommodating large $CO_2$ sources due to favorable economics with carbon capture credits and its non-reliance on local, dispersed and small scale-sources of nutrients.

Embodiments of the present invention may have the potential to be transformational in that it may provide a new, highly efficient pathway for biofuels production options, that can reduced the nation's dependence on both domestic and foreign oil perhaps by up to about 64 billion barrel crude equivalents annually and can be rapidly deployed. A CAT bacteria-based system may provide the transportation sector with 'drop-in' fuels, such as biodiesel, aviation fuel, and gasoline perhaps providing a leap forward in commercial deployment relative to algae. The uniqueness of the CAT bacterial process may occur in three areas—process, product, and integration with a $CO_2$ source.

Embodiments of the present invention may provide a CAT bacteria process which may employ a unique shuttling system based on sulfur, which may be abundant on the earth. It may not use any expensive rare earth elements or perhaps even any organic redox shuttles. Unlike other bacteria-based systems that may use metal-containing solids, a CAT bacteria system may be gas- and liquid phase perhaps avoiding the complications of transfer of fine solids in (and between)

reactors, which may allow superior mixing and bacteria growth. By replacing solid particle based electron shuttling systems with soluble gases the tendency for biofilm on the shuttle substrate may be eliminated.

In embodiments, a feature of a CAT bacteria concept may employ a dual reactor system with perhaps different bacteria and different conditions thereby allowing for optimization of each bacteria growth. A system can modify $CO_2$ conditions to meet $H_2S$ production in a controlled manner to produce the optimum production of biomass.

Unlike photosynthesis-based biofuels production process, a CAT-based process may not be driven by photosynthesis. Unlike photosynthesis-based algae processes that may capture less or no $CO_2$ during low light conditions, thus perhaps complicating their integration with a variety of $CO_2$ sources, even with the use of artificial lighting, a CAT bacteria process may provide a controlled and perhaps even constant capture of $CO_2$ independent of lighting conditions, thus maximizing yield.

Bacteria can be harvested separately to produce biofuels that may meet industry specifications and may maximize the recovery of high value components, such as paraffin or together for lipid yield and biofuel production. CAT bacteria produced lipid yields may be comparable to algae and may be used in petroleum replacement products as well as biofuels such as biodiesel. The SRB bacteria can produce one quarter of its extractable mass as paraffins, which may have high value use in ozone proofing rubber and as a hot climate asphalt additive. Heterotrophic bacteria may have similar growth rates to algae, perhaps affording reasonable lipid yields.

The footprint of the CAT bacteria-based system may be projected to be lower than ethanol or open algae production systems (acres/ton of biomass) perhaps by a factor of about 50 compared to open algae production systems and a factor of about 10 compared with algae photobioreactors that require external lighting at significant operating costs perhaps resulting in less restriction on CAT siting.

A CAT bacteria-based concept can be produced in reasonably sized modules to meet varying sized $CO_2$ sources and may be compatible with commercially available lipid extraction and biodiesel production process, thereby allowing for rapid deployment.

Embodiments of the present invention may be self sufficient with respect to nutrients by converting a non-oil portion of a biomass into nutrients needed in the process. Other microbial processes that require external nutrient sources may be limited in scale due to the quantity of local nutrients available and the infrastructure cost to deliver it to the $CO_2$ source, perhaps restricting potential deployment sites.

In a CAT bacteria-based process, $CO_2$ can be selectively removed from the flue gas and any remaining flue gas, $CO_2$ and other flue gas species can be can be handled through existing plant stack and plant infrastructure (fans), affording easy retrofit.

Unlike open algae systems with high evaporative water losses, the embodiments of the present invention may employ recycling in an essentially closed loop. Makeup water can also be supplied by low rank coal upgrading processes or even by produced waters from the coalbed methane and oil and gas production.

The bacteria-based concept may be unique and may offer many attributes making it a transformational and market disrupting technology with rapid development and broad and rapid commercial deployment options.

The bioreactor media and gas conditions may impact the carbon assimilation rates of selected chemoautotrophs and these chemoautotrophs may impact the product composition related to biofuels and petroleum replacement products. Other process data needed may include bacteria/strains growth rates, extractable product characteristics, water quality treatment needs, and perhaps even baseline data for operation of bioreactors.

Species/strains of bacteria for use in the anaerobic sulfur reducing bioreactor and the chemoautotrophic $CO_2$ capture bioreactor may be determined experimentally based on process efficiencies of bacteria species known to perform the required assimilations. Bacteria evaluated for use in the sulfur reducing system may include *Desulfovibrio* ssp. The chemoautotrophic bacteria evaluated for use in the $CO_2$ capture bioreactor may include species from three (3) genera, *Thiobacillus* ssp, *Paracoccus* ssp, and perhaps even *Thiovulum* ssp. *Thiobacillus denitrificans* may be the primary candidate to be well characterized and may have been shown to be effective for sulfide oxidation. Other species from the *Thiobacillus* genus such as *T. thioparus, T. caldus* and *T. hydrothermalis* may also prove to be effective. Several available species from the *Paracoccus* and *Thiovulum* geneses are expected to be effective.

Bioreactors may be used to culture the bacteria to determine perhaps the most prolific species for the capture of $CO_2$ and reactor sizing. Optimal conditions within the bioreactors can be determined for each bacteria/strain using a number of environmental variables. Process parameters may be controlled using computer systems equipped to maintain constant conditions and perhaps to identify small changes in biomass production. The impact of nutrient combinations and sources on bacteria populations and assimilations can also be determined.

Bacteria cultures for use in the sulfur reducing bioreactor and the chemoautotrophic $CO_2$ capture bioreactor may be acquired from the American Type Culture Collection (ATCC) bacteria performance/engineering design. Chemoautotrophic bacteria cultures can be evaluated for maximum carbon fixation rates and perhaps even lipid production based on optimal conditions including but not limited to: temperature, pH, nutrient concentrations (micro- and macronutrients), $H_2S$ concentrations, inorganic carbon concentrations (e.g., $CO_2$, $HCO_3^-$ or $CO_3^{2-}$ depending on pH), inorganic ion concentrations, bacterial cell densities, or the like. Sulfur reducing bacteria can be assessed for maximizing the conversion of $SO_4^{2-}$ to $H_2S$ based on optimal environmental conditions in the bioreactor. Lipids associated with biomass generated by the bacteria may be quantified and characterized to determine an amount and quality of extractable product for end-use applications such as biofuels and petroleum replacement products. Water quality may impact assimilation rates in the bioreactor systems. Tests using a range of soluble salt concentrations can be conducted using the candidate bacteria/strains. Water exiting the bioreactor can be tested to determine the need for treatment, particularly when using wastewaters or alternate sources such as coal bed methane produced waters.

Optimization studies may determine the conditions required to maximize the production of biomass perhaps using the most prolific bacterium. Deployment may use the highest biomass producers under the most favorable environmental conditions identified. Methods can be integrated to improve biomass quantity and quality including but not limited to: (1) harvesting point; (2) optimizing $CO_2$ incorporation into the bioreactor solution to reach maximum biomass production; and perhaps even (3) the use of an electrical current to improve the kinetics of $CO_2$ assimilation. The biomass may be harvested during an exponential growth phase of the bacteria. An optimal concentration for harvesting bacterial biomass may be determined experimentally for each of the species/strain of bacteria. Other considerations for optimization may include methods of injecting $CO_2$ into the bioreactor solution using either gas sparging (bubbles) or perhaps even membrane infuser systems (microscopic bubbles), such as being developed by Carbon2Algae (C2A). Higher levels of solution $CO_2$ may enhance biomass yields to a maximum for each bacteria/strain evaluated (potentially about 3 to about 5 times higher with membrane infusers). Another potential optimization agent may be associated with the use of an electrical current to enhance bio-reactions. The use of electrical current may have been shown to enhance chemoautotrophic bacteria growth rate in an anaerobic system and may improve oxidation of sulfides in an oxidizing bioreactor resulting in higher assimilation of $CO_2$ and corresponding increased biomass yield. Electron use by bacteria may not have a direct relationship with sulfate reduction as electrons can reduce $SO_4^{-2}$ directly without bacterial involvement and therefore may be unlikely to improve bio-reactions in the anaerobic system. Biomass may be harvested from the chemoautotrophic bioreactors at intervals near the peak in the growth phase of the bacteria. The impact of biomass removal on growth rate of the bacteria may be determined with the objective of establishing the optimum removal point that will not detract from the continued pace of $CO_2$ assimilation. $CO_2$ can be incorporated into the chemoautotrophic bioreactor using injection methods. The rate of $CO_2$ assimilation can be determined for each injection method evaluated. The maximum solution concentrations of $CO_2$ can be determined along with the corresponding rate of $CO_2$ assimilation.

The conventional method of harvesting the bacteria from the bioreactors may be by filtration, followed by a drying step, an oil extraction step and perhaps even the production of the biodiesel. It may be desirable to assess advanced technologies being developed by others as to their applicability to any core chemoautotrphic bacteria carbon capture and biofuels process. There may be a number of advanced harvesting techniques that are being developed for other biofuels and other industries that may have promise with the process of the embodiments of the present invention. Most harvesting methods available for microbial process may have been originally developed for animal tissues and plant materials. The development of harvesting processes may depend on the conditions of the culture media, nature of the bacteria cells, or perhaps even the type of extract desired. The following process steps may be examined: (1) killing or forced dormancy of the bacteria can be achieved by several approaches, including heating, cooling, foaming, addition of chemical agents such as acid, base, sodium hypochlorite, enzymes, or antibiotics; (2) the technologies available to separate the bacteria from the bulk culture media may involve centrifugation, rotary vacuum filtration, pressure filtration, hydrocycloning, flotation, skimming, and perhaps even sieving. These technologies can be applied in conjunction with other techniques, such as addition of flocculating agents, or coagulating agents. The relevant parameters to be determined may include bacteria size, density and tendency to coalesce into larger flocks; (3) water may need to be removed from the harvested bacteria to prevent the occurrence of lipolysis or perhaps even metabolically the breakdown of glycerides into free fatty acids within bacteria cells. Various technologies may be used for the drying step, such as perhaps direct and even indirect methods; and perhaps even (4) after dewatering, the lipids and fatty acids may be separated from the bacterial mass, or even extracted. It may be important during the extraction to prevent auto-oxidative degradation and perhaps even to minimize the presence of artifacts to ensure high yield of glycerides. Available approaches may include but are not limited to centrifugation, high pressure homogenization, filtration, as well as solvents such as methanol or ethanol extraction. Solvent extraction can be a combination of mechanical and chemical cell lysis, or cell disruption. Mechanical methods of lysis as well as chemical methods and enzymes may also be examined.

Figure 6A:
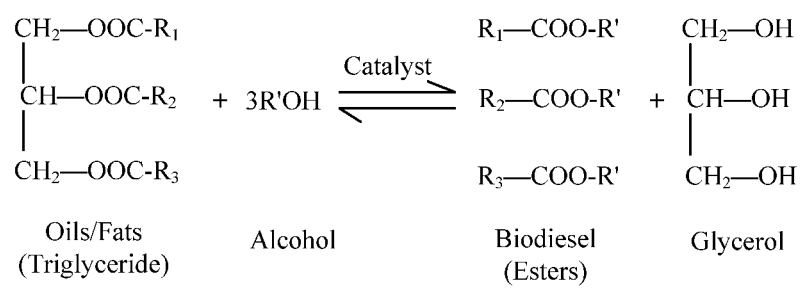
FIG. 6A is an example of catalytical transesterification in accordance with embodiments of the present invention.

It may be desirable to assess the application of advanced technology for biodiesel production as well as other bio-products, such as green plastics. From a chemical point of view, biodiesel may be mainly composed of fatty acids mono-alkyl esters. It may be produced from triglycerides (the major compounds of oils and fats) with short chain alcohols perhaps via catalytic transesterification as shown in the example of FIG. 6A. Depending on the type of catalyst adopted, the methods for biodiesel production can be classified as conventional or perhaps even enzyme based. For the former, alkali catalysts, such as KOH and NaOH, with the combination of acid catalyst, such as phosphorus acid, may be used. For the latter, enzyme, such as lipase, may be used as catalyst. The effort can determine if these techniques are applicable to various embodiments of the present invention. Extracted microbial oil can also be applied for the production of green plastics including packaging films mainly for use as shopping bags, containers and paper coatings, disposable items such as razors, utensils, diapers, cosmetic containers and cups, as well as medical surgical garments, upholstery, carpets, packaging, compostable bags and lids or tubs, or the like. Investigations may be performed to explore several factors related to effective green-plastic production. The quality of resultant green plastics can be determined through ASTM D6866. The major component of the residue may be the cell debris leftover from oil and fatty acid extraction. Like algae, cell debris of the bacteria may contain cellulose and perhaps even a variety of glycoproteins. These components may be analyzed and evaluated for end use applications.

Bacteria can be produced from various types of lipid materials, including paraffins and glycerides. In the early stages of bacteria harvesting, the glyceride, paraffinic, and other lipid materials from these processes may require some chemical characterization. Characterization of the glyceride material prior to transesterification may be important to help determine the potential yield of the eventual biodiesel conversion process. This may involve using thin layer or column chromatography to evaluate the polar vs. non-polar lipids content. Glyceride lipids may be transesterified with methanol (to perhaps biodiesel), further characterization can be performed using a gas chromatography/mass spectrometry techniques to provide a fatty acid type and distribution for the material. The standardized characterization of bio-diesel for use as a transportation fuel may follow ASTM method D6751.

Control of dual reactors and perhaps even the resultant products under continuous operation may be assessed. These may represent critical items for commercial deployment. In addition, the operational issues such as fouling and perhaps even scaling may need to be known and may be resolved prior to progressing to the next development phase.

Embodiments of the present invention may include a plant design, development and perhaps even validation may consist of integration of two bacteria bioreactors and verification of operational parameters. A system may be based on two independent bacterial systems perhaps providing essential sulfur looping to sustain carbon capture at a constant and predictable rate. It may be desirable to size, determine and optimize operational conditions perhaps to ensure efficient coupling of the systems within the operational regime. Bacterial species selection may be key in this effort, perhaps due to the highly specific needs of individual and consortium bacterial species. Design parameters may specify fluid stream flow rates and chemical composition for control of nutrient addition, pH, $H_2S$ recovery and delivery systems, operational temperatures for the subsystem reactors, and perhaps even working volume for desired output parameters for each of the subsystems. Also, the system design may consider comparison of state-of-the-art membrane gas infusion techniques in comparison with traditional gas sparging. In addition, techniques developed for harvesting microalgae may be evaluated for bacteria, and may have to be modified accordingly.

Embodiments of the present invention may include but are not limited to vessel sizing, line sizing, input/output identification, system parameter monitoring specification, and perhaps even biomass density calculations. This may include design of $H_2S$ recovery units for the control of toxic $H_2S$ levels in the primary sulfur reducing reactor, and may even include delivery units for the infusing of $H_2S$ into the secondary carbon fixing reactor. Also, $CO_2$ species control through pH and monitoring of these species online and integrated into the control system may be designed. This may involve assigning process control steps to develop relationships between $CO_2$ uptake, carbon cycling in the reactor, $H_2S$ to $CO_2$ uptake, and perhaps even the best source reduction or increase to accomplish these reactions in a controlled manner while maximizing carbon conversion. Gas feed to the reaction vessels can be designed with the flexibility to evaluate multiple gas sparging and perhaps even membrane based gas infusion technologies. This may include comparison of existing technologies for extraction of oils from bacteria and perhaps even determination of the most suitable choice for the application, or the development of new technologies to tailor the extraction technique to bacterial applications.

System performance may determine a system's flexibility to evaluate external processing techniques such as but not limited to membrane gas infusion, cyclonic separation of biomass, high pressure homogenization and perhaps even additional state-of-the-art bacteria based oil extraction techniques, and operational improvements may be evaluated for reducing bio-fouling.

A system startup and shakedown may be completed in several stages. The system may be run with sterile water for operational checks. Next, the seed reactors may be run to provide biomass for analysis to ensure that the species may be produced and conform to bench-scale data. Then each of the large bioreactors may be run independently to ensure working parameters meet the expected operational regimes. Finally integrated operation of the combined systems may be performed and operational conditions determined for steady state operation. Initially operation of the seed vessel may focus on the use of traditional gas sparging methods. A seed vessel may be fitted with state-of-the-art membrane gas infusion technology and the operational parameters at different pressure, temperature and nutrient feed rates may be quantified to define scaling factors for unit operation. The parameters needed to recover the system from an upset in operational conditions may be determined, such as a loss in productivity in the sulfur reducing reactor or a sudden change in pH in both tanks as well as perhaps quantifying the system integrity over longer term runs for stability. Biomass may be produced and even recovered using industry standard dewatering techniques and then the effective biomass can be tested for adaptability of algae based oil extraction techniques and the two sub-streams of biomass and oil can be analyzed for acceptability and conformity to bench-scale results. Additional information on bio-fouling can be evaluated during the production runs and vessel liners to prohibit microbial attachment.

The biodiesel module may be tested to ascertain the performance of the reactor design and reaction control, separator design and control, parameter monitoring, as well as reactor and separator scale-up. The yield of biodiesel may be compared with the results for the other feed materials. The quality of resultant biodiesel can be examined according to ASTM D 6751 in terms of flash point, water and sediment, carbon residue, sulfated ash, density, kinematic viscosity, sulfur, cetane number, cloud point, copper corrosion, acid number, free glycerin, total glycerin, density and perhaps even iodine number; the results can be compared with petroleum diesel fuel.

Embodiments of the present invention may provide CAT based system integration and deployment strategies. It may be desirable to assess the scalability of the CAT process using modeling approaches, the efficiency and cost modeling results for the integration of the CAT process for various sized $CO_2$ sources, an infrastructure/product market assessment, including the impacts of regulations in the $CO_2$ emissions area and the legislative initiatives for enhanced biofuels production and an engineering scale-up and perhaps even estimate a pre-commercial-scale module of the CAT process.

In order to affect scale-up of the CAT biodiesel/bioproducts production process, the modeling of the system may be necessary. Operational test data can be used to refine the preliminary model both functionally and quantitatively. In order to understand the commercial transition and the impact on both the facility supplying the $CO_2$ and the biodiesel/bioproducts market, CAT process integration at the $CO_2$ generating site can be conducted. Three scenarios may be addressed: (1) Fossil-fuel fired utility that generates electric power at a nominal 570 MW scale and need to be retrofitted with 65% carbon capture; (2) Refinery that may have a $CO_2$ source, $H_2S$ source and easy integration into the refinery products; and perhaps even (3) Industrial-scale facility, such as cement, lime, or fertilizer manufacturing facility, with a local biodiesel/bioproducts market.

The modeling and system integration can be based on the CAT process model performance. The fossil-fuel fired utility case can expand on the preliminary mass balance as discussed below. The base case power plant may produce at least about 4 million tons/yr of $CO_2$ emissions before about 65% capture.

Embodiments of the present invention may address the CAT process as a 'drop in' biofuels process into a conventional biodiesel plant and may even evaluate the impact of different amounts of carbon capture on plant efficiency and costs. The use of the CAT process residue biomass for various products as feed for aquaculture and livestock feed and nutrient source for process can be assessed. A similar analysis of the integration of the CAT process into a refinery that has a $CO_2$ source, an $H_2S$ source to perhaps reduce the load requirements for the CAT process and which could provide easy integration into the biocrude refining to various refinery products. The model input may use about 4 million tons of CO₂ as the base refinery input parameter to perhaps study the bioprocess integration with a refinery application and about 65% CO₂ capture. In addition, it may be desirable to examine a smaller-scale application such as an industrial-scale cement, lime or fertilizer manufacturing facility, with perhaps a local biodiesel/bioproducts market. For the cement plant, a CO₂ emissions of about 0.5 million tons may be considered. There are several local markets for biodiesel, including at mines, railroad fueling stations, or even municipality and perhaps even school district markets.

The integration may be based on the biocrude yield from the pilot-scale tests and the quality of biodiesel and other co-produced products. The configuration can also include the use of the bio-residue product as a nutrient source or alternatively produce other bioproducts, such as aquaculture and livestock feed supplements.

Figure 6B:
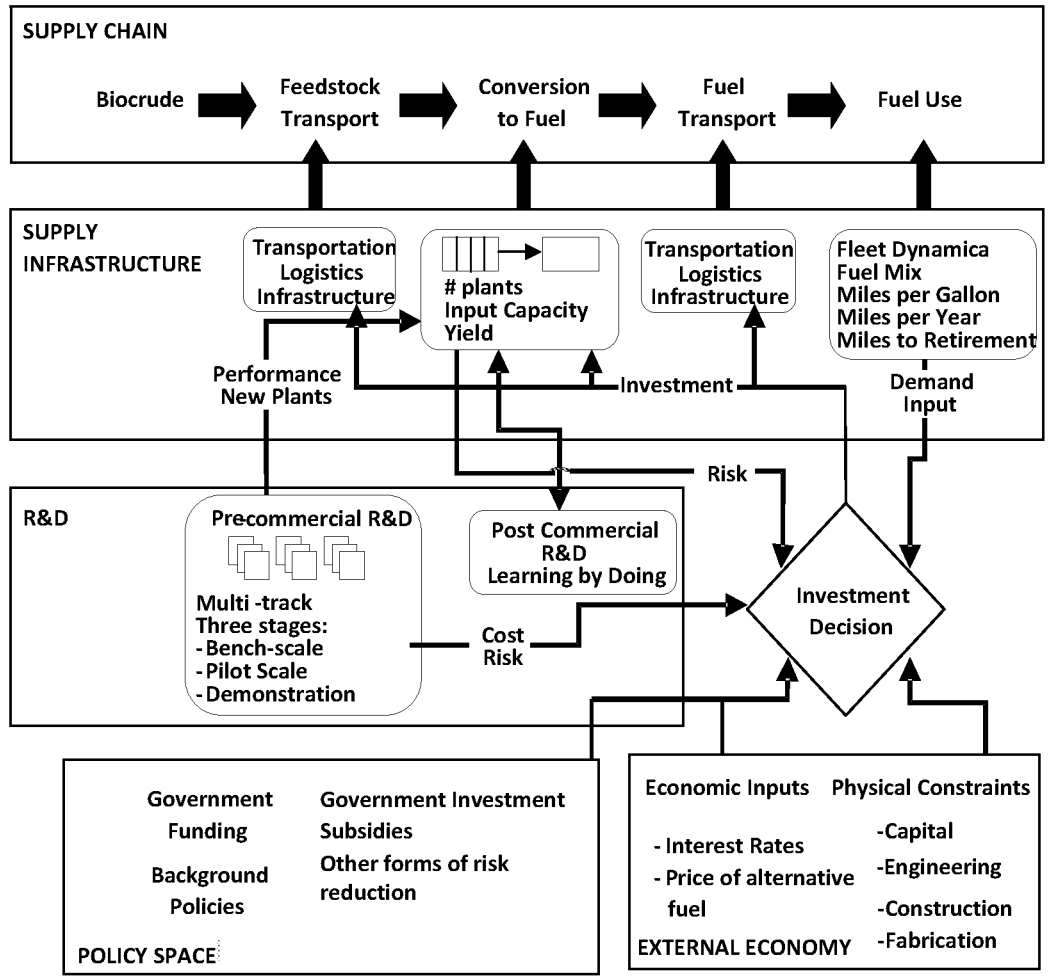
FIG. 6B is an example of a system dynamic modeling for market penetration in accordance with embodiments of the present invention.

Embodiments of the present invention may address the system dynamic modeling for CAT biodiesel market penetration. An example of the strategy model analysis for CAT biodiesel, modeled after an ethanol model by NREL, is presented in FIG. 6B. Following a similar protocol, a similar model and analysis can be developed and performed for CAT biodiesel. As explained above, there may not be a "one-size-fits-all" solution. CAT biodiesel market penetration can be built upward as in the NREL model (FIG. 6B) from the policy and the external economy basis. The policy space can include government funding opportunities, legislative mandates such as the Renewable Portfolio Standard, low carbon fuel as well as government (both federal and state) subsidies in the form of tax credits and perhaps even loan guarantees. The legislative policies may also include the impact on the CO₂ source, such as carbon capture and storage legislation, carbon credits and impact of alternate carbon capture options on parasitic power and cost of electricity. The external economy factors that may include interest rates and price of competing technologies may assess the government policies tax credits, and subsidies. Note that international agreements may also put pressure on the U.S. to reduce GHG. It may be desirable to examine the supply infrastructure, pre-commercial R&D and perhaps even evaluation of the investment potential for each type of application. Deployment at industrial-scale facilities may need a distributed biodiesel market-based, while larger-scale CO₂ sources siting strategy may allow for infrastructure compatible fuel distribution. All of these analysis components may be needed to minimize risk for investment and permitting decisions that allows for commercial deployment.

Embodiments of the present invention may include preliminary evaluations of the preliminary mass balance for the system, preliminary system energy balance, projected composition of the biodiesel that can be produced from microbial materials, preliminary cost estimates for the CAT bacterial biofuel process, and perhaps even a preliminary mass balance for the system.

A CAT process may involve a symbiosis of two types of bacteria with very different attributes and metabolic requirements. Chemolithotrophic bacteria may have been shown to fix inorganic carbon in conjunction with oxidation of sulfides. When lactate, a relatively common nutrient, may be used, one possible metabolism is listed as follows:

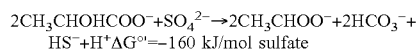

A possible metabolism for the sulfide oxidation may include:

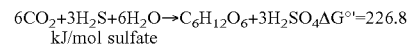

In addition, it has been reported that CO₂ fixing rate at the sulfide oxidation bio-reactor may be 0.132 g CO₂/g Bacteria/hr. In the sulfate reduction bio-reactor, nutrient (lactate) consumption rate may be about 2.1 g Lactate/g Bacteria/hr, and sulfate reduction rate may be about 1.2 g Sulfate/g Bacteria/hr. This may leads to about 1.9 g Nutrient (lactate) for about 1.0 g CO₂ to be captured.

Figure 7:
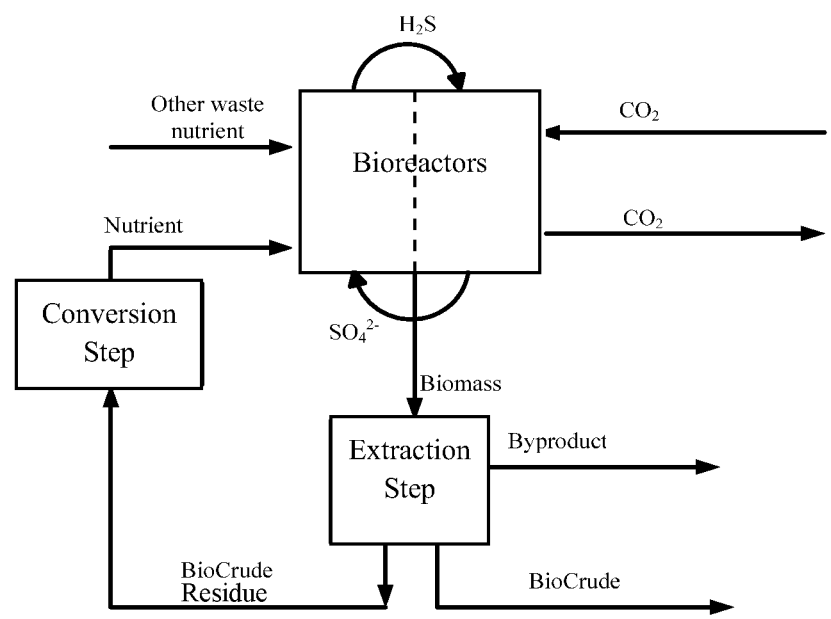
FIG. 7 is an example of a schematic diagram of the drop-in CAT process integrated into about 600 MWe power plant with the flow rate unit of Mlb/hr (the biomass conversion (e.g., the amount of $CO_2$ converted to biomass) is assumed to be 95%) in accordance with embodiments of the present invention.
Figure 8:
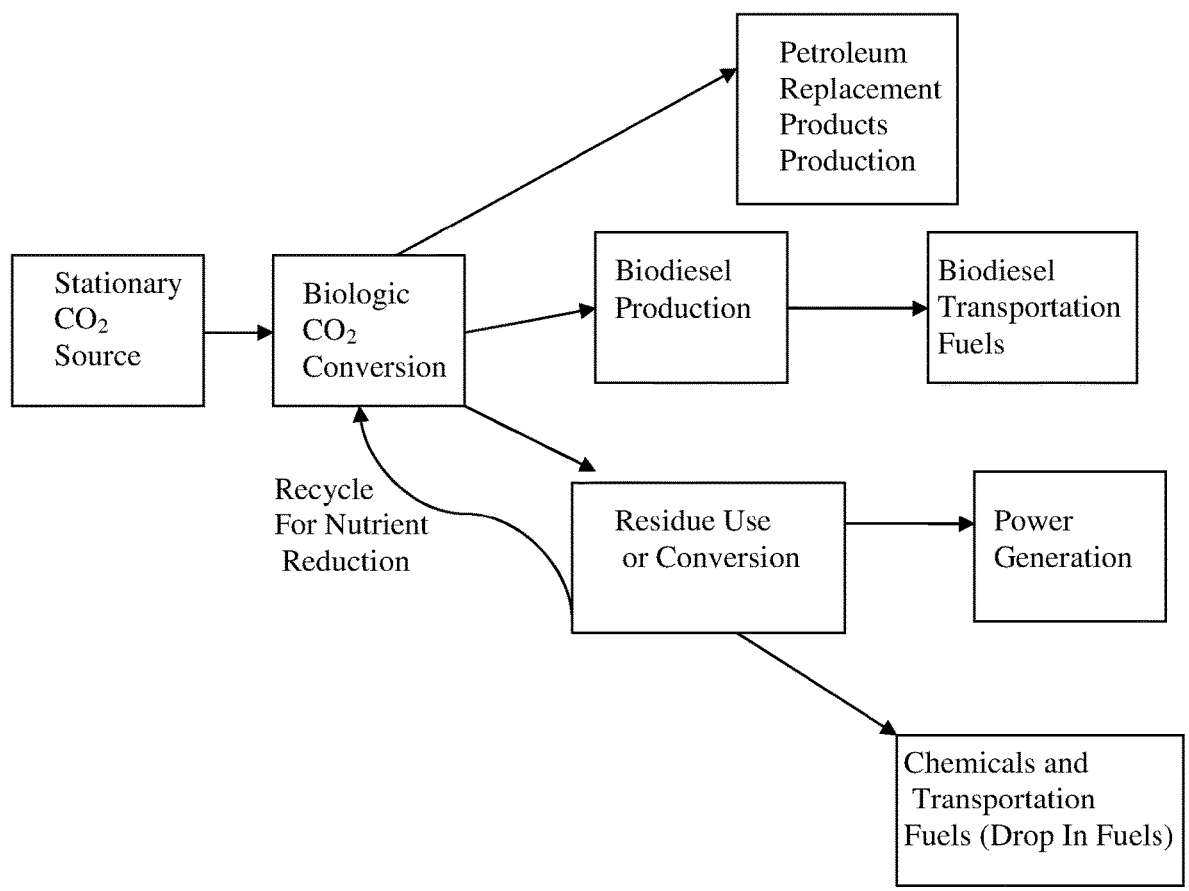
FIG. 8 is an example of a general system in accordance with embodiments of the present invention.

A schematic of a typical about 570 MWe coal-fired power plant is shown in FIG. 7. Depending on the fuel characteristics, a coal-fired power plant may emit approximately 4 million tons of CO₂ annually. The plant may also have a limited amount of SO₂ and NOx emissions that might be beneficial in a CAT process. FIG. 7 represents the mass balance around the drop-in CAT process integrated into the power plant. CO₂ emission from a 603 MW PRB power plant may be about 1195 Mlb/hr. If it is assumed that about 65% of CO₂ can be captured by CAT process, around about 1476 Mlb/hr nutrient will be needed for the bacteria cultivation according to the aforementioned calculation, i.e., about 1.9 g Nutrient (lactate) for about 1.0 g CO₂ to be captured. Assuming that about 95% of CO₂ is converted to biomass in the bioreactors, biomass production rate can be about 2140 Mlb/hr, about 30% of which can be used for biodiesel production. The rest (about 70%), i.e., about 1476 Mlb/hr, can be recycled to the bioreactors as the nutrients through the conversion step, thereby meeting the system nutrient needs.

In embodiments, to generate about 603 MW of electricity, the PRB coal and air input may be about 633 and about 5038 Mlb/hr, respectively, with a flue gas amount of about 5671 Mlb/hr. After sulfur and ash removal, the amount of cleaned flue gas may be about 4659 Mlb/hr, about 25.6 wt % of which is CO₂, i.e., about 1195 Mlb/hr. Assuming that about 65% of CO₂ will be captured by CAT process, about 1476 Mlb/hr nutrients may be needed for the bacteria cultivation according to the preliminary study, i.e., about 1.9 g nutrient (lactate) for about 1.0 g CO₂ to be captured. Assuming that about 95% biomass conversion in the bioreactors, biomass production rate can be about 2140 Mlb/hr, about 30% of which can be used for biodiesel production. The rest (about 70%), i.e., about 1476 Mlb/hr, can be recycled to the bioreactors as the nutrients through the conversion step, thereby perhaps eliminating the external nutrient supply. When other waste nutrients may be available, there may be additional residue available to partially replace consumption.

Biodiesel can contain no more than about six or about seven fatty acid esters. This renders it possible to estimate the properties of each pure component, and then compute the mixture properties based on the available mixing rules. The properties of anticipated biodiesel fuel may exceed industry targets (see Table 1).

TABLE 1

WRI Proposed Targets

| Component | Target |
|---|---|
| Liquid fuel type: diesel fuel, JP-8 aviation fuel and/or higher octane fuels for four-stroke internal combustion engines | 51 cetane Biodiesel Fuel |
| Anticipated liquid fuel energy density | 42 MJ/kg |
| Anticipated liquid fuel heat of vaporization | 0.06 MJ/kg |

TABLE 1-continued

WRI Proposed Targets

| Component | Target |
|---|---|
| Anticipated liquid fuel-energy-out to photon/electrical energy-in of the envisioned system | >63% |
| Rare earth elements or organic redox shuttles | Economical at distributed generation, industrial facility and central power plant scales |

Nutrients for bacteria cultivation may be about $0.50/kg with the lactate price close to about $0.50/kg. Energy requirements for bacteria harvesting based on the mechanical methods can be approximately $0.10/kg. For microbial oil extraction, the cost could be around $0.60/kg when methanol is used as extraction solvent with the price may be about $0.3/kg. The cost for biodiesel production may be about $0.20/kg through the conventional method. It may be important to note that methanol used for microbial extraction may also serve as the only reactant besides bio-oil for the biodiesel production. Thus, total cost for the biodiesel may be about $1.20/kg, or about $3.87/gallon. The cost estimation is summarized in Table 2. Similar analyses may be needed for site specific deployment of the CAT process.

TABLE 2

Estimation of the Production Cost (US$/kg) of Biodiesel from Bacterial-Based Oils

| Cost structure | Nutrients | Bacteria harvesting | Bacaterial oil extraction | Biodiesel production | Total cost (per kg) |
|---|---|---|---|---|---|
| In US$ | $0.50 | $0.10 | $0.40 | $0.20 | $1.20 |

With the expected energy density of biodiesel to be about 42 MJ/kg, the cost of fuel could be about $0.30/MJ, or about $3.0\times10^{-5}$/Btu based on about 1 MJ equal to about 948 BTU.

Biodiesel may generally contain no more than about six or about seven fatty acid esters enabling estimating the properties of each pure component, and then computing the mixture properties based on the available mixing rules. No rare earth elements may be used and organic redox shuttles involved may not be easily deployed economically at large scale. Integration with coal fired power plants may enable use of low grade thermal energy and may even provide a ready supply of nutrients.

The biodiesel fuel can be a next generation renewable fuels that may easily integrate into the U.S. current biofuel refining and distribution infrastructure at both large central plants and local distributed scale pzalants, perhaps while not diverting resources currently utilized for food production. In fact, one end product can be domestic fertilizer to lower costs for domestic farm livestock and produce production. The proposed concept may not use photosynthetic autotrophic production. If the over 2.5 billion metric tons of $CO_2$ emitted in the U.S. each year from coal power plants may be converted to bio-oils and transportation fuels, this technology may present the potential to avoid the net expenditures for imported crude oil (and petroleum products) estimated to reach about $377,000,000,000 U.S. dollars by 2030. This may have a tremendously positive impact of the U.S. trade deficit, and may be even better if exports result.

The technology may leverage synthetic biology and metabolic engineering advances to modify microbiological metabolic pathways and perhaps even develop novel biological systems that can directly utilize electrons and reduced metal ions as a source of reducing equivalents for conversion of $CO_2$ to liquid fuels. At an overall system efficiency>about 60%, the technology may effectively and efficiently convert $CO_2$ into a diesel fuel. The concept may entail the development of a sulfur-based Calvin cycle variant that accepts reducing equivalents from regenerable agents other than Photosystems I and II or even directly from solar current. In addition, the CAT process may be a specifically engineered system and set of bioreactors to provide an ecosystem environment that cultures bacterium and may be self-sustaining resulting in a robust organism engineered ecosystem well suited for commercial scale integration with coal power plants. This may allow easy access to organisms and biosynthetic routes to conduct independent, unbiased validation. The various species created may be readily analyzed with existing technology. The technology may be forward thinking in that the nutrient sources used for stimulation and augmentation of the biologic growth may be supplemented with biomass recycling and waste stream organics, perhaps resulting in creative approaches and innovation to design, development, and integrated practical and economically viable production systems. By well-engineered integration, the concept may maximize energy and water conservation, may maximize efficiency and may even minimize costs. Further the system and major components may be well-known equipment within various industry sectors making it scalable, robust, and perhaps even relatively straightforward to maintain and operate by traditional skilled workforce with only minor training.

As can be easily understood from the foregoing, the basic concepts of the present invention may be embodied in a variety of ways. It involves both biological conversion techniques as well as devices to accomplish the appropriate biological converter. In this application, the biological conversion techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "reactor" should be understood to encompass disclosure of the act of "reacting"—whether explicitly discussed or not—and, conversely, were there effectively disclosure of the act of "reacting", such a disclosure should be understood to encompass disclosure of a "reactor" and even a "means for reacting." Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

U.S. PATENT APPLICATION PUBLICATIONS

| Publication Number | Publication Date | Name of Patentee or Applicant of cited Document |
|---|---|---|
| 20100120104 A1 | 2010 May 13 | Reed |

Non-Patent Literature Documents

Akoh, C. C., S. Chang, G. Lee and J. Shaw, "Enzymatic approach to biodiesel production," J. Agric. Food Chem., 55, 8995-9005, 2007.

Antoni, D., V. V. Zverlov, and W. H. Schwarz, "Biofuels from microbes," Appl. Microbiol. Biot., 77, 23-35, 2007.

Bland, A., J. Newcomer, T. Zhang, K. Sellakumar, "Pilot testing of WRI's novel mercury control technology by recombustion thermal treatment of coal", Report to U.S. Department of Energy, Contract No. DE-FC26-98FT40323 Task 79, June 2009.

Certick, M. and S. Shimizu, "Review: biosynthesis and regulation of microbial polyunsaturated fatty acid production," J. Biosci. Bioeng., 87, 1-14, 1999.

Certik, M. and R. Horenitzky, "Supercritical $CO_2$ extraction of fungal oil containing y-linolenic acid," Biotechnol. Tech., 13, 11-15, 1999.

Chen, G., "A microbial polyhydroxyalkanoates (PHA) based bio- and materials industry," Chem. Soc. Rev., 38, 2434-2446, 2009.

Ciferno, J., "Pulverized coal oxycombustion power plants—final results" (revised), U.S. Department of Energy, National Energy Technology Laboratory, Nov. 1, 2007.

Cooney, M. J., E. Roschi, I. W. Marison, C. Comninellis, and U. Von Stockar, "Physiologic studies with the sulfate reducing bacterium *Desulfovibrio desulfuricans*: Evaluation for use in a biofuel cell," Enzym. Microb. Tech., 8, 358-365, 1996.

Dasu, B. N., and K. L. Sublette, "Microbial Removal of sulfur dioxide from a gas stream with net oxidation to sulfate," Appl. Biochem. Biotech., Vol 20/21, 207-220, 1989.

Davis, J. B., "Paraffinic hydrocarbons in the sulfate reducing bacterium *Desulfovibrio desulfuricans*," Chem. Geol., 3, 155-160, 1968.

Demirbas, Ayhan, "Sustainable cofiring of biomass with coal," Energy Conversion and Management, Vol 44, 1465-1479

Dhar, B. R., and K. Kirtania, "Excess methanol recovery in biodiesel production process using a distillation column: a simulation study," Chemical Engineering Research Bulletin, 13, 45-50, 2009.

DOE/NETL, "Cost and performance baseline for fossil energy plants-Vol. 1: bituminous coal and natural gas to electricity," DOE/NETL-2007/1281, May 2007, Revision 1, August 2007.

Garces, R., R. Alvarez-Ortega, E. Martinez-Force, S. Cantisan, "Lipid characterization in vegetative tissues of high saturated fatty acid sunflower mutants," J. Agric. Food Chem., 47, 78-82, 1999.

Green Econometrics, "Understanding the cost of solar energy," http://greenecon.net/understanding-the-cost-of solarenergy/energy_economics.html, 2007.

GTM Research, "Transitioning from 1st generation to advanced biofuels," a white paper from Enterprise Florida and GTM Research, February 2010.

Howard, E. E., "Systems and methods for large-scale production and harvesting of oil-rich algae," PCT/US2007/006466, WO2007/109066 A1.

Kadam, K. L., "Environmental implications of power generation via coal-microalgae cofiring," Energy, Vol 27, 905-922, 2002.

Kelly, D. P, "Thermodynamic aspects of energy conservation by chemolithotrophic sulfur bacteria in relation to the sulfur oxidation pathways," Arch Microbial, 171, 219-229, 1999

Li, Q., W. Du, and D. Liu, "Perspectives of microbial oils for biodiesel production," Appl. Microbiol. Biot., 80, 749-756, 2008.

Mona, K. G., H. O. Sanaa, and M. A. Linda, "Single cell oil production by *Gordonia* spp. DG using agro-industrial wastes," World J. Microbiol. Biotechnol., 24, 1703-1711, 2008.

Monteiro, M. R., A. R. P. Ambrozin, L. M. Lião, and A. G. Ferreira, "Critical review on analytical methods for biodiesel characterization," Talanta, 77, 593-605, 2008, Parawira, W., "Biotechnological production of biodiesel fuel using biocatalyzed transesterification: A review," Cr. Rev. Biotechn., 29, 82-93, 2009.

Rabus, R., T. A. Hansen and F. Widdel, "Dissimilatory sulfate- and sulfur-reducing prokaryotes," Prokaryotes, 2, 659-768, 2006.

Scott, K. M., and C. M. Cavanaugh, "$CO_2$ uptake and fixation by endosymbiotic chemoautotrophs from the bivalve *Solemya velum*," Appl. Environ. Microb., 73, 1174-1179, 2007.

Shively, J. M., G. van Keulen, and W. G. Meijer, "Something from almost nothing: carbon dioxide fixation in chemoautotrophs," Annu. Rev. Microbiol, 52, 191-230, 1998.

Thurmond, W., Algae 2020: Algal Biofuels Demand Drivers, Players, Business Models, Markets & Commercialization Outlook, 1st edition, 2009, www.emerging-market.com.

van Lier, R. J. M., C. J. N. Buisman, and N. L. Piret, "THIOPAQ® technology: versatile high-rate biotechnology for the mining and metallurgical industries," Proceedings of the TMS Fall Extraction and Processing Conference, v 3, p 2319-2328, 1999.

Yuan, W., A. C. Hansen, and Q. Zhang, "Predicting the physical properties of biodiesel for combustion modeling," T. ASAE, 46, 1487-1493, 2003.

Zhang, T., and L. T. Fan, "Significance of dead-state-based thermodynamics in designing a sustainable process," Design for Energy and the Environment—Proceedings of the Seventh International Conference on the Foundations of Computer-Aided Process Design, Eds., M. M. El-Halwagi and A. A. Linninger, CRC Press, Boca Raton, Fla., pp. 233-241, 2010.

Zhang, X., R. Luo, Z. Wang, Y. Deng, and G. Chen, "Application of (R)-3-hydroxyalkanoate methyl esters derived from microbial polyhydroxyalkanoates as novel biofuels," Biomacromolecules, 10, 707-711, 2009.

Thus, the applicant(s) should be understood to have support to claim and make a statement of invention to at least: i) each of the biological conversion devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for biologically converting inorganic carbon to useful products comprising the steps of:
   containing inorganic carbon emissions from a source;
   introducing said inorganic carbon emissions from said source into a sulfide oxidation bioreactor;
   introducing oxygen into said sulfide oxidation bioreactor;
   biologically producing biomass, sulfate, and sulfites in said sulfide oxidation bioreactor;
   transferring said sulfate and said sulfites produced in said sulfide oxidation bioreactor to a sulfur reducing bioreactor;
   utilizing said sulfate and said sulfites in said sulfur reducing bioreactor;
   biologically producing biomass and hydrogen sulfide in said sulfur reducing bioreactor;
   recycling said hydrogen sulfide from said sulfur reducing bioreactor to said sulfide oxidation bioreactor;
   utilizing said recycled hydrogen sulfide in said sulfide oxidation bioreactor in said step of biologically producing said biomass, sulfate, and sulfites in said sulfide oxidation bioreactor;
   extracting at least some biomass, lipids and paraffin from said sulfide oxidation bioreactor and said sulfur reducing bioreactor; and
   producing products from said biomass, said lipids, and said paraffin extracted from said sulfide oxidation bioreactor and said sulfur reducing bioreactor.

2. A method for biologically converting inorganic carbon to useful products according to claim 1 wherein said sulfide oxidation bioreactor comprises chemoautotrophic bacteria.

3. A method for biologically converting inorganic carbon to useful products according to claim 1 wherein said sulfur reducing bioreactor comprises sulfate reducing bacteria.

4. A method for biologically converting inorganic carbon to useful products according to claim 1 and further comprising the step of biologically converting un-extracted biomass in said sulfide oxidation bioreactor and said sulfur reducing reactor to a nutrient material.

5. A method for biologically converting inorganic carbon to useful products according to claim 4 wherein said nutrient material comprises lactate.

6. A method for biologically converting inorganic carbon to useful products according to claim 4 and further comprising the step of recycling nutrients to both said sulfide oxidation bioreactor and said sulfur reducing bioreactor.

7. A method for biologically converting inorganic carbon to useful products according to claim 1 and further comprising the step of recovering un-converted nutrient sources.

8. A method for biologically converting inorganic carbon to useful products according to claim 7 and further comprising the step of dewatering said un-converted nutrient sources.

9. A method for biologically converting inorganic carbon to useful products according to claim 1 wherein said step of introducing said oxygen into said sulfide oxidation bioreactor comprises the step of providing oxygen from said source.

10. A method for biologically converting inorganic carbon to useful products according to claim 1 and further comprising the step of recovering oxygen and carbon dioxide from said sulfide oxidation bioreactor.

11. A method for biologically converting inorganic carbon to useful products according to claim 1 and further comprising the step of dewatering said biomass extracted from said sulfide oxidation bioreactor and said sulfur reducing bioreactor.

12. A method for biologically converting inorganic carbon to useful products according to claim 1 wherein said products are selected from a group consisting of methane, hydrogen, alcohol, fertilizer, feedstock, fuel, transportation fuel, bioenergy, food, biofuel, biodiesel, aviation fuel, gasoline, military fuels, ethanol, plastics, animal feed, and food amendments.

13. A method for biologically converting inorganic carbon to useful products according to claim 1 and further comprising the step of recovering non-extractable biomass from said sulfide oxidation bioreactor and said sulfur reducing bioreactor.

14. A method for biologically converting inorganic carbon to useful products according to claim 1 wherein said source of said inorganic carbon emissions is selected from a group consisting of power generation sources, cement producing plants, coal refineries, oil refineries, refineries, lime producing plants, non-power generation sources, coal-fired power plants, natural gas-fired power plants, generation fuel cells, and combustion power plants.

15. A method for biologically converting inorganic carbon to useful products according to claim 1 and further comprising the step of reusing said biomass.

* * * * *